United States Patent
Kyle et al.

(10) Patent No.: US 8,399,486 B2
(45) Date of Patent: Mar. 19, 2013

(54) BENZENESULFONYL COMPOUNDS AND THE USE THEREOF

(75) Inventors: Donald J. Kyle, Newtown, PA (US); Jiangchao Yao, Monmouth Junction, NJ (US)

(73) Assignee: Purdue Pharma L.P., Stamford, CT (US)

( * ) Notice: Subject to any disclaimer, the term of this patent is extended or adjusted under 35 U.S.C. 154(b) by 519 days.

(21) Appl. No.: 12/595,066

(22) PCT Filed: Apr. 8, 2008

(86) PCT No.: PCT/US2008/004490
§ 371 (c)(1),
(2), (4) Date: Oct. 8, 2009

(87) PCT Pub. No.: WO2008/124118
PCT Pub. Date: Oct. 16, 2008

(65) Prior Publication Data
US 2011/0098281 A9    Apr. 28, 2011

Related U.S. Application Data

(60) Provisional application No. 60/907,571, filed on Apr. 9, 2007.

(51) Int. Cl.
*A61K 31/445* (2006.01)
*C07D 211/56* (2006.01)
*C07D 211/58* (2006.01)
*C07D 211/98* (2006.01)

(52) U.S. Cl. .................................. 514/317; 546/244
(58) Field of Classification Search .................. None
See application file for complete search history.

(56) References Cited

U.S. PATENT DOCUMENTS

| | | | |
|---|---|---|---|
| 4,034,098 A | 7/1977 | Archibald et al. |
| 4,131,680 A | 12/1978 | Archibald et al. |
| 4,145,427 A | 3/1979 | Langbein et al. |
| 5,028,519 A | 7/1991 | Morigaki et al. |
| 5,688,960 A | 11/1997 | Shankar |
| 5,696,267 A | 12/1997 | Reichard et al. |
| 5,723,490 A | 3/1998 | Tung |
| 5,739,135 A | 4/1998 | Biller et al. |
| 5,827,875 A | 10/1998 | Dickson, Jr. et al. |
| 5,866,589 A | 2/1999 | Romero et al. |
| 5,936,089 A | 8/1999 | Carpino et al. |
| 5,965,559 A | 10/1999 | Faull et al. |
| 5,972,963 A | 10/1999 | Merriman et al. |
| 5,981,490 A | 11/1999 | Baxter et al. |
| 5,998,412 A | 12/1999 | Broka et al. |
| 6,011,035 A | 1/2000 | Snutch et al. |
| 6,124,341 A | 9/2000 | Tasker et al. |
| 6,130,220 A | 10/2000 | Broka et al. |
| 6,136,827 A | 10/2000 | Caldwell et al. |
| 6,136,839 A | 10/2000 | Isakson et al. |
| 6,143,744 A | 11/2000 | Broka et al. |
| 6,248,739 B1 | 6/2001 | Turner et al. |
| 6,262,046 B1 | 7/2001 | Alker et al. |
| 6,267,945 B1 | 7/2001 | Zamponi |
| 6,281,227 B1 | 8/2001 | Choi-Sledeski et al. |
| 6,294,533 B1 | 9/2001 | Snutch et al. |
| 6,303,620 B1 | 10/2001 | Hansen et al. |
| 6,310,059 B1 | 10/2001 | Snutch |
| 6,316,623 B1 | 11/2001 | Swayze et al. |
| 6,323,217 B2 | 11/2001 | Peglion et al. |
| 6,350,760 B1 | 2/2002 | Bakshi et al. |
| 6,355,631 B1 | 3/2002 | Achard et al. |
| 6,376,506 B1 | 4/2002 | Broka et al. |
| 6,380,224 B1 | 4/2002 | Dax et al. |
| 6,384,080 B1 | 5/2002 | Oku et al. |
| 6,387,897 B1 | 5/2002 | Snutch |
| 6,423,519 B1 | 7/2002 | Bergnes et al. |
| 6,458,790 B2 | 10/2002 | Palucki et al. |
| 6,492,375 B2 | 12/2002 | Snutch |
| 6,525,042 B1 | 2/2003 | Kobayashi et al. |

(Continued)

FOREIGN PATENT DOCUMENTS

CA    2 579 886 A1    3/2006
EP    1 249 233 A1    10/2002

(Continued)

OTHER PUBLICATIONS

Triggle. Biochemical Pharmacology, 2007, 74, 1-9.*

(Continued)

*Primary Examiner* — Noble Jarrell

(74) *Attorney, Agent, or Firm* — Sterne, Kessler, Goldstein & Fox P.L.L.C.

(57) ABSTRACT

The invention relates to pyrrolidinyl, piperidinyl, and hexahydroazepinyl compounds of Formula I: and pharmaceutically acceptable salts, prodrugs, or solvates thereof, wherein $R^1$, $R^2$, Z and m are defined as set forth in the specification. The invention is also directed to the use compounds of Formula I to treat a disorder responsive to the blockade of calcium channels, and particularly N-type calcium channels. Compounds of the present invention are especially useful for treating pain.

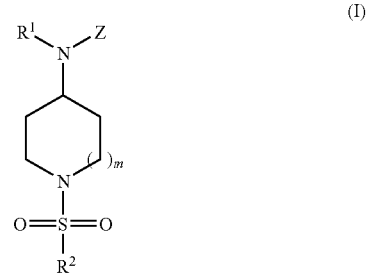

(I)

51 Claims, No Drawings

U.S. PATENT DOCUMENTS

| | | |
|---|---|---|
| 6,559,146 B1 | 5/2003 | Annoura et al. |
| 6,562,978 B1 | 5/2003 | Imamura et al. |
| 6,613,572 B2 | 9/2003 | Matsuoka et al. |
| 6,617,322 B2 | 9/2003 | Snutch |
| 6,664,273 B2 | 12/2003 | Burnett et al. |
| 6,667,319 B2 | 12/2003 | Stamford et al. |
| 6,667,342 B1 | 12/2003 | Clarke et al. |
| 6,683,093 B2 | 1/2004 | Barta et al. |
| 6,699,891 B1 | 3/2004 | Kawanishi et al. |
| 6,734,176 B2 | 5/2004 | Achard et al. |
| 6,743,790 B2 | 6/2004 | Klingler et al. |
| 6,750,228 B1 | 6/2004 | Barta et al. |
| 6,841,552 B1 | 1/2005 | Dax et al. |
| 6,894,063 B2 | 5/2005 | Greenlee et al. |
| 6,946,476 B2 | 9/2005 | Stamford et al. |
| 6,962,917 B2 | 11/2005 | Davies et al. |
| 6,987,188 B2 | 1/2006 | Dax et al. |
| 6,995,144 B2 | 2/2006 | Ozaki et al. |
| 6,998,401 B2 | 2/2006 | Annoura et al. |
| 7,045,636 B2 | 5/2006 | Palani et al. |
| 7,056,942 B2 * | 6/2006 | Hildesheim et al. ......... 514/411 |
| 7,067,507 B2 * | 6/2006 | Pulley et al. .................. 514/183 |
| 7,109,207 B2 | 9/2006 | Burnett et al. |
| 7,132,443 B2 | 11/2006 | Haffner et al. |
| 7,183,413 B2 | 2/2007 | Lin et al. |
| 7,205,408 B2 | 4/2007 | Davies et al. |
| 7,262,206 B2 | 8/2007 | Heckel et al. |
| 7,268,150 B2 | 9/2007 | Hayakawa et al. |
| 7,405,210 B2 | 7/2008 | Bradley et al. |
| 7,449,482 B2 | 11/2008 | Cheng et al. |
| 7,534,892 B2 | 5/2009 | Nakatani |
| 7,544,690 B2 | 6/2009 | Sekiguchi et al. |
| 7,598,391 B2 | 10/2009 | Murray et al. |
| 7,786,308 B2 | 8/2010 | Drutu et al. |
| 7,868,205 B2 | 1/2011 | Moradei et al. |
| 7,951,801 B2 | 5/2011 | Hepperle et al. |
| 7,964,613 B2 * | 6/2011 | Matsubara et al. ......... 514/309 |
| 2001/0029258 A1 | 10/2001 | Snutch |
| 2001/0056184 A1 | 12/2001 | Noda et al. |
| 2002/0013310 A1 | 1/2002 | Choi-Sledeski et al. |
| 2002/0055457 A1 | 5/2002 | Janus et al. |
| 2002/0094989 A1 | 7/2002 | Hale et al. |
| 2002/0115863 A1 | 8/2002 | Patel et al. |
| 2002/0128476 A1 | 9/2002 | Marquis, Jr. et al. |
| 2002/0151712 A1 | 10/2002 | Lin et al. |
| 2003/0045530 A1 | 3/2003 | Snutch |
| 2003/0092732 A1 | 5/2003 | Yu et al. |
| 2003/0130265 A1 | 7/2003 | Pouzet et al. |
| 2003/0158186 A1 | 8/2003 | Malik et al. |
| 2003/0176461 A1 | 9/2003 | Egle et al. |
| 2003/0216380 A1 | 11/2003 | Josien et al. |
| 2003/0225060 A1 | 12/2003 | Ujjainwalla et al. |
| 2003/0229067 A1 | 12/2003 | Castelhano et al. |
| 2003/0232808 A1 | 12/2003 | Kobayashi et al. |
| 2003/0236283 A1 | 12/2003 | Radeke et al. |
| 2004/0006081 A1 | 1/2004 | Burrows et al. |
| 2004/0006089 A1 | 1/2004 | Thurieau et al. |
| 2004/0014745 A1 | 1/2004 | Yamada et al. |
| 2004/0067947 A1 | 4/2004 | Wathen et al. |
| 2004/0102431 A1 | 5/2004 | Boss et al. |
| 2004/0102450 A1 | 5/2004 | Ewing et al. |
| 2004/0152692 A1 | 8/2004 | Dhanak et al. |
| 2004/0186148 A1 | 9/2004 | Shankar et al. |
| 2004/0224901 A1 | 11/2004 | Chaturvedula et al. |
| 2005/0014789 A1 | 1/2005 | Andrews et al. |
| 2005/0032773 A1 | 2/2005 | Piot-Grosjean et al. |
| 2005/0043535 A1 | 2/2005 | Aissaoui et al. |
| 2005/0070534 A1 | 3/2005 | Carruthers et al. |
| 2005/0085518 A1 | 4/2005 | Dai et al. |
| 2005/0119266 A1 | 6/2005 | Shi et al. |
| 2005/0153980 A1 | 7/2005 | Schadt et al. |
| 2005/0165065 A1 | 7/2005 | Pajouhesh et al. |
| 2005/0197336 A1 | 9/2005 | Anandan et al. |
| 2005/0239796 A1 | 10/2005 | Thurieau et al. |
| 2005/0245573 A1 | 11/2005 | Neitzel et al. |
| 2005/0250784 A1 | 11/2005 | Anandan et al. |
| 2005/0277647 A1 | 12/2005 | Link et al. |
| 2005/0282831 A1 | 12/2005 | Beauglehole et al. |
| 2006/0014761 A1 | 1/2006 | Morgan et al. |
| 2006/0014783 A1 | 1/2006 | Aissaoui et al. |
| 2006/0058287 A1 | 3/2006 | Axten et al. |
| 2007/0043081 A1 | 2/2007 | Bur et al. |
| 2007/0104644 A1 | 5/2007 | Cuthbertson et al. |
| 2007/0179180 A1 | 8/2007 | Busch-Petersen et al. |
| 2007/0293477 A1 | 12/2007 | Casillas et al. |
| 2008/0103139 A1 | 5/2008 | Ishizuka et al. |
| 2009/0048227 A1 | 2/2009 | Chakravarty et al. |
| 2009/0105249 A1 | 4/2009 | Benjamin et al. |
| 2009/0239910 A1 | 9/2009 | Chen et al. |
| 2009/0306136 A1 | 12/2009 | Matsumura et al. |
| 2010/0022595 A1 | 1/2010 | Chen et al. |
| 2010/0216841 A1 | 8/2010 | Barrow et al. |
| 2010/0311792 A1 | 12/2010 | Shao et al. |
| 2011/0098281 A9 | 4/2011 | Kyle et al. |

FOREIGN PATENT DOCUMENTS

| | | |
|---|---|---|
| EP | 1 254 895 A1 | 11/2002 |
| EP | 1 702 916 A1 | 9/2006 |
| GB | 1 445 595 A | 8/1976 |
| GB | 2 000 136 A | 1/1979 |
| GB | 2 352 240 A | 1/2001 |
| JP | 5-201971 A | 8/1993 |
| JP | 2005/154380 A | 6/2005 |
| JP | 2005/179351 A | 7/2005 |
| JP | 2006-83133 A | 3/2006 |
| JP | 2006-83137 A | 3/2006 |
| WO | WO 90/15600 A2 | 12/1990 |
| WO | WO 93/22283 A1 | 11/1993 |
| WO | WO 97/45119 A1 | 12/1997 |
| WO | WO 99/01451 A1 | 1/1999 |
| WO | WO 99/44596 A2 | 9/1999 |
| WO | WO 99/47508 A1 | 9/1999 |
| WO | WO 00/37059 A2 | 6/2000 |
| WO | WO 00/42011 A1 | 7/2000 |
| WO | WO 01/04087 A1 | 1/2001 |
| WO | WO 01/24786 A1 | 4/2001 |
| WO | WO 01/44179 A1 | 6/2001 |
| WO | WO 01/45709 A1 | 6/2001 |
| WO | WO 01/49670 A1 | 7/2001 |
| WO | WO 01/70708 A1 | 9/2001 |
| WO | WO 01/81308 A2 | 11/2001 |
| WO | WO 01/87839 A1 | 11/2001 |
| WO | WO 02/22592 A2 | 3/2002 |
| WO | WO 02/24649 A1 | 3/2002 |
| WO | WO 02/28346 A2 | 4/2002 |
| WO | WO 02/42257 A1 | 5/2002 |
| WO | WO 02/49648 A1 | 6/2002 |
| WO | WO 02/070479 A1 | 9/2002 |
| WO | WO 03/013527 A1 | 2/2003 |
| WO | WO 03/022277 A1 | 3/2003 |
| WO | WO 03/024456 A1 | 3/2003 |
| WO | WO 03/045977 A2 | 6/2003 |
| WO | WO 03/048154 A1 | 6/2003 |
| WO | WO 03/051868 A1 | 6/2003 |
| WO | WO 03/059265 A2 | 7/2003 |
| WO | WO 03/079025 A2 | 9/2003 |
| WO | WO 03/084542 A1 | 10/2003 |
| WO | WO 2004/009549 A2 | 1/2004 |
| WO | WO 2004/055006 A1 | 7/2004 |
| WO | WO 2004/058709 A1 | 7/2004 |
| WO | WO 2004/058736 A1 | 7/2004 |
| WO | WO 2004/083167 A1 | 9/2004 |
| WO | WO 2004/105750 A1 | 12/2004 |
| WO | WO 2004/111014 A1 | 12/2004 |
| WO | WO 2005/011697 A2 | 2/2005 |
| WO | WO 2005/030209 A1 | 4/2005 |
| WO | WO 2005/044797 A1 | 5/2005 |
| WO | WO 2005/090296 A2 | 9/2005 |
| WO | WO 2005/095418 A1 | 10/2005 |
| WO | WO 2005/097779 A1 | 10/2005 |
| WO | WO 2006/030211 A2 | 3/2006 |
| WO | WO 2006/040181 A1 | 4/2006 |
| WO | WO 2006/105127 A2 | 10/2006 |
| WO | WO 2006134481 * | 12/2006 |
| WO | WO 2007/052843 A1 | 5/2007 |
| WO | WO 2007/067617 A2 | 6/2007 |
| WO | WO 2007/075524 A2 | 7/2007 |

| | | | |
|---|---|---|---|
| WO | WO 2007/110449 A1 | 10/2007 | |
| WO | WO 2007/118853 A1 | 10/2007 | |
| WO | WO 2007/118854 A1 | 10/2007 | |
| WO | WO 2008/050200 A1 | 5/2008 | |
| WO | WO 2008/051873 A2 | 5/2008 | |
| WO | WO 2008/061016 A1 | 5/2008 | |
| WO | WO 2009/040659 A2 | 4/2009 | |

OTHER PUBLICATIONS

Kehlet. The Lancet, 2006, 367, 1618-25.*
"Alzheimer's disease," Aetna InteliHealth, accessed at: http://www.intelihealth.com/IH/ihtIH/WSIHW000/8303/9117/195703.html?d=dmtHealthAZ, accessed on Jul. 1, 2008, 4 Pages.
Banker, G.S. and Rhodes, C.T., eds., *Modern Pharmaceutics, Third Edition, Revised and Expanded*, p. 451 & 596, Marcel Dekker, Inc., United States (1996).
Bergeron, R.J., et al., "Polyamine Analogue Regulation of NMDA MK-801 Binding: A Structure-Activity Study," *J. Med. Chem.* 39:5257-5266, American Chemical Society, United States (1996).
Bingham, A.L., et al., "Over one hundred solvates of sulfathiazole," *Chem. Commun. 2001*:603-604, The Royal Society of Chemistry, England (2001).
Bleicher, K.H., et al., "Parallel Solution- and Solid-Phase Synthesis of Spiropyrrolo-Pyrroles as Novel Neurokinin Receptor Ligands," *Bioorg. Med. Chem. Lett. 12*:3073-3076, Elsevier Science Ltd., England (2002).
Bobich, J.A., et al., "Incubation of nerve endings with a physiological concentration of $A\beta_{1-42}$ activates CaV2.2(N-Type)-voltage operated calcium channels and acutely increases glutamate and noradrenaline release," *J. Alzheimer's Dis. 6*:243-255, IOS Press, Netherlands (2004).
Brower, V., "New paths to pain relief," *Nat. Biotechnol. 18*:387-391, Nature America Publishing, United States (2000).
Bundgaard, H., "Means to Enhance Penetration: Prodrugs as a means to improve the delivery of peptide drugs," *Adv. Drug Deliv. Rev. 8*:1-38, Elsevier Science Publishers, B.V., Netherlands (1992).
Caira, M.R., et al., "Preparation and Crystal Characterization of a Polymorph, a Monohydrate, and an Ethyl Acetate Solvate of the Antifungal Fluconazole," *J. Pharm. Sci. 93*:601-611, Wiley-Liss, Inc. and the American Pharmacists Association, United States (2004).
Castellano, A., et al., "Cloning and Expression of a Neuronal Calcium Channel β Subunit," *J. Biol. Chem. 268*:12359-12366, The American Society for Biochemistry and Molecular Biology, Inc., United States (1993).
Catterall, W.A., et al., "International Union of Pharmacology. XLVIII. Nomenclature and Structure-Function Relationships of Voltage-Gated Calcium Channels," *Pharmacol, Rev. 57*:411-425, The American Society for Pharmacology and Experimental Therapeutics, United States (2005).
Caulfield, W.L., et al., "The First Potent and Selective Inhibitors of the Glycine Transporter Type 2," *J. Med. Chem. 44*:2679-2682, American Chemical Society, United States (2001).
Chemical Abstracts Database, Registry No. 397244-98-3, Chemical Name: Benzenesulfonamide, N-[1-[(2,6-dimethoxyphenyl)methyl]-4-piperidinyl]-N-propyl-3-(trifluoromethyl)-, published Mar. 1, 2002.
Chemical Abstracts Database, Registry No. 402929-10-6, Chemical Name: Benzenesulfonamide, N-cyclopropyl-N-[1-(phenylmethyl)-4-piperidinyl]-, published Mar. 27, 2002.
Cox, B., "Calcium Channel Blockers and Pain Therapy," *Curr. Rev. Pain 4*:488-498, Current Science Inc., United States (2000).
Dubel, S.J., et al., "Molecular cloning of the α-1 subunit of an ω-conotoxin-sensitive calcium channel," *Proc. Natl. Acad. Sci. USA. 89*:5058-5062, National Academy of Sciences, United States (1992).
Eidelman, O. and Cabantchik, Z.I., "Continuous monitoring of transport by fluorescence on cells and vesicles," *Biochim. Biophys. Acta 988*:319-334, Elsevier Science Publishers B.V., Netherlands (1989).
Filer, C.N., "The Preparation and Characterization of Tritiated Neurochemicals," in *Isotopes in the Physical and Biomedical Sciences. vol. 1 Labelled Compounds (Part A)*, Buncel, E. and Jones, J.R., eds., p. 156-192, Elsevier Science Publishers B.V., Netherlands (1987).

Finney, Z.G. and Riley, T.N., "4-Anilidopiperidine Analgesics. 3. 1-Substituted 4-(Propananilido)perhydroazepines as Ring-Expanded Analogues," *J. Med. Chem. 23*:895-899, American Chemical Society, United States (1980).
Gould, R.J., et al., "Antischizophrenic drugs of the diphenylbutylpiperidine type act as calcium channel antagonists," *Proc. Natl. Acad Sci. USA 80*:5122-5125, National Academy of Sciences, United States (1983).
Grigg, R. and Coulter, T., "Sequential 1,3-Dipolar Cycloaddition-Palladium Catalysed Cyclisation. A Powerful New Tactical Combination.," *Tetrahedron Lett. 32*:1359-1362, Pergamon Press plc., England (1991).
Grinvald, A., "Real-Time Optical mapping of Neuronal Activity: From Single Growth Cones to the Intact Mammalian Brain," *Ann. Rev. Neurosci. 8*:263-305, Annual Reviews Inc., United States (1985).
Grinvald, A., et al., "Fluorescence Monitoring of Electrical Responses From Small Neurons and Their Processes," *Biophys. J. 42*:195-198, Biophysical Society, United States (1983).
Grinvald, A., et al., "Improved Fluorescent Probes for the Measurement of Rapid Changes in Membrane Potential," *Biophys. J. 39*:301-308, Biophysical Society, United States (1982).
Grynkiewicz, G., et al., "A New Generation of $Ca^{2+}$ Indicators with Greatly Improved Fluorescence Properties," *J. Biol. Chem. 260*:3440-3450, The American Chemical Society of Biological Chemists, Inc., United States (1985).
Hamill, O.P., et al., "Improved Patch-Clamp Techniques for High-Resolution Current Recording from Cells and Cell-Free Membrane Patches," *Pflügers Arch. 391*:85-100, Springer-Verlag, Germany (1981).
Hansen, H.C., et al., "Multistep Solution-Phase Parallel Synthesis of Spiperone Analogues," *Bioorg. Med. Chem. Letts. 10*:2435-2439, Elsevier Science Ltd., England (2000).
Hanson, G.R., "Analgesic, Antipyretic and Anti-inflammatory Drugs," in *Remington: The Science and Practice of Pharmacy. vol. II*, $19^{th}$ Edition, pp. 1196-1221, Gennaro, A., ed., Lippincott Williams & Wilkins, United States (1995).
Hosford, D.A., et al., "A radiohistochemical measure of [$^3$H]TCP binding to the activated NMDA-receptor-gated ion channel in rat brain," *Brain Res. 516*:192-200, Elsevier Science Publishers B.V., Netherlands (1990).
Hu, L.-Y., et al., "The Discovery of [1-(4-Dimethylamino-benzyl)-piperidin-4-yl]-[4-(3,3-dimethylbutyl)-phenyl]-(3-methyl-but-2-enyl)-Amine, an N-type $Ca^{+2}$ Channel Blocker with Oral Activity for Analgesia," *Bioorg. Med. Chem. 8*:1203-1212, Elsevier Science, England (2000).
Hu, L-Y., et al., "Structure-Activity Relationship of N-Methyl-N-Aralkyl-Peptidylamines as Novel N-Type Calcium Channel Blockers," *Bioorg. Med. Chem. Lett. 9*:2151-2156, Elsevier Science Ltd., England (1999).
Hu, L-Y., et al., "Synthesis of a Series of 4-Benzyloxyaniline Analogues as Neuronal N-Type Calcium Channel Blockers with Improved Anticonvulsant and Analgesic Properties," *J. Med. Chem. 42*:4239-4249, American Chemical Society, United States (1999).
Hunskaar, S., et al., "Formalin test in mice, a useful technique for evaluating mild analgesics," *J. Neurosci. Meth. 14*:69-76, Elsevier Publishers B.V., Netherlands (1985).
Insel, P.A., "Analgesic-Antipyretic and Antiinflammatory Agents and Drugs Employed in the Treatment of Gout," in *Goodman & Gilman's The Pharmacological Basis of Therapeutics*, $9^{th}$ Edition, p. 617-657, Hardman, J.G., et al., eds., The McGraw-Hill Companies, Inc., United States (1996).
Ito, M., "Long-Term Depression," *Ann. Rev. Neurosci. 12*:85-102, Annual Reviews Inc., United States (1989).
Janis, R.A., and Triggle, D.J., "Drugs Acting on Calcium Channels," in *Calcium Channels: Their Properties, Functions, Regulations, and Clinical Relevance*, Hurwitz et al., eds., CRC Press, London, England, pp. 195-249 (1991).
Kakeya, N., et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4- yl)-(Z)-2-methoxyiminoacetamido]-3-methyl-3-cephem-4-carboxylic Acid," *Chem. Pharm. Bull. 32*:692-698, Pharmaceutical Society of Japan, Japan (1984).

Karikomi, M., et al., "A novel synthesis of 3-aminoazetidines by ring transformation of 2-(bromomethyl)aziridines," *Tetrahedron Lett. 41*:10295-10298, Elsevier Science Ltd., Netherlands (2000).

Khosravani, H. and Zamponi, G.W., "Voltage-Gated Calcium Channels and Idiopathic Generalized Epilepsies," *Physiol. Rev. 86*:941-966, the American Physiological Society, United States (Jul. 2006).

Kim, H-L., et al., "Rat brain expresses an alternatively spliced form of the dihydropyridine-sensitive L-type calcium channel α2 subunit," *Proc. Natl. Acad. Sci. USA. 89*:3251-3255, National Academy of Sciences, United States (1992).

Kim, S.H. and Chung, J.M., "An experimental model for peripheral neuropathy produced by segmental spinal nerve ligation in the rat," *Pain 50*:355-363, Elsevier Science Publishers B.V., Netherlands (1992).

Koch, W.J., et al., "cDNA Cloning of a Dihydropyridine-sensitive Calcium Channel from Rat Aorta. Evidence for the Existence of Alternatively Spliced Forms," *J. Biol. Chem. 265*:17786-17791, The American Society for Biochemistry and Molecular Biology, Inc., United States (1990).

Levine, J. and Taiwo, Y., "Inflammatory pain," in *Textbook of Pain*, 3rd Edition, pp. 45-56, Wall, P.D. and Melzack, R., eds., Churchill Livingstone, United Kingdom (1994).

Lin, Z., et al., "Identification of Functionally Distinct Isoforms of the N-Type $Ca^{2+}$ Channel in Rat Sympathetic Ganglia and Brain," *Neuron 18*:153-166, Cell Press, United States (1997).

Loew, L.M. and Simpson, L.L., "Charge-Shift Probes of Membrane Potential. A Probable Electrochromic Mechanism for p-Aminostyrylpyridinium Probes on a Hemispherical Lipid Bilayer," *Biophys. J. 34*:353-365, Biophysical Society, United States (1981).

Lowe, J.A., et al., "Nuclear Variations of Quinuclidine Substance P Antagonists: 2-Diphenylmethyl-1-azabicyclo[3.2.2]nonan-3-amines," *Bioorg. Med. Chem. Letts. 3*:921-924, Pergamon Press Ltd., England (1993).

Lukyanetz, E.A., et al., "Selective Blockade of N-Type Calcium Channels by Levetiracetam," *Epilepsia 43*:9-18, Blackwell Publishing, United States (2002).

Marecek, J.F. and Burrows, C.J., "Synthesis of an Optically Active Spermine Macrocycle, (S)-6-(Hydroxymethyl)-1,5,10,14-Tetraazacyclooctadecane, and Its Complexation to ATP," *Tetrahedron Lett. 27*:5943-5946, Pergamon Journals Ltd., Great Britain (1986).

Martin, Y.C., et al., "Do Structurally Similar Molecules Have Similar Biological Activity?" *J. Med. Chem. 45*:4350-4358, American Chemical Society, United States (2002).

Moreno Davila, H., "Molecular and Functional Diversity of Voltage-Gated Calcium Channels," *Ann. NY Acad. Sci. 868*:102-117, The New York Academy of Sciences, United States (1999).

Murakami, M., et al., "Modified sympathetic regulation in N-type calcium channel null-mouse," *Biochem. Biophys. Res. Comm. 354*:1016-1020, Elsevier Inc., United States (Jan. 2007).

Neher, E. and Sakmann, B., "The Patch Clamp Technique. A simple procedure can easily isolate ion channels on cell membranes. Its Nobel Prize-winning developers explain what the technique has revealed about cellular signaling," *Sci. Ameri. 266*:44-51, Scientific American, United States (1992).

Nielsen, K.J., et al., "Structure-activity relationships of ω-conotoxins at N-type voltage-sensitive calcium channels," *J. Mol. Recognit. 13*:55-70, John Wiley & Sons, Ltd., United States (2000).

Nielsen, N.M. and Bundgaard, H., "Glycolamide Esters as Biolabile Prodrugs of Carboxylic Acid Agents: Synthesis, Stability, Bioconversion, and Physicochemical Properties," *J. Pharm. Sci. 77*:285-298, the American Pharmaceutical Association, United States (1988).

Nuglisch, J., et al., "Protective Effect of Nimodipine Against Ischemic Neuronal Damage in Rat Hippocampus Without Changing Postischemic Cerebral Blood Flow," *J. Cereb. Blood Flow Metab. 10*:654-659, Raven Press Ltd., United States (1990).

Piró, J., et al., "Asymmetric synthesis of β-pseudopeptides from chiral 3,4-aziridinolactams," *Tetrahedron Asymmetry 13*:995-1004, Elsevier Science Ltd., England (2002).

Pragnell, M., et al., "Cloning and tissue-specific expression of the brain calcium channel β-subunit," *FEBS Lett. 291*:253-258, Elsevier Science B.V., Netherlands (1991).

Rolland, C., et al., "G-Protein-Coupled Receptor Affinity Prediction Based on the Use of Profiling Dataset: QSAR Design, Synthesis, and Experimental Validation," *J. Med. Chem. 48*:6563-6574, American Chemical Society, United States (2005).

Romero, M., et al., "New Advances in the Field of Calcium Channel Antagonists: Cardiovascular Effects and Structure-Activity Relationships," *Curr. Med. Chem. Cardiovasc. Hematol. Agents. 1*:113-141, Bentham Science Publishers Ltd., United Arab Emirates (2003).

Russell, M.G.N., et al., "3-[(Piperidin-1-yl)propyl]indoles as Highly Selective $h5-HT_{1D}$ Receptor Agonists," *J. Med. Chem. 42*:4981-5001, American Chemical Society, United States (1999).

Sasikumar, T.K., et al., "Tetrahydroisoquinolines as MCH-R1 antagonists," *Bioorg. Med. Chem. Lett. 16*:4917-4921, Elsevier Ltd., England (Jul. 2006).

Scarpa, A., "Measurements of Cation Transport with Metallochromic Indicators," *Meth. Enzymol. 56*:301-338, Academic Press, United States (1979).

Schwartz, A., et al., "Receptors for Calcium Antagonists," *Am. J. Cardiol. 62*:3G-6G, Cahners Publishing Company, United States (1988).

Seko, T., et al., "L-Cysteine Based N-type Calcium Channel Blockers: Structure-Activity Relationships of the C-Terminal Lipophilic Moiety, and Oral Analgesic Efficacy in Rat Pain Models," *Bioorg. Med. Chem. Letts. 12*:2267-2269, Elsevier Science Ltd., England (2002).

Seko, T., et al., "Structure-Activity Study and Analgesic Efficacy of Amino Acid Derivatives as N-Type Calcium Channel Blockers," *Bioorg. Med. Chem. Letts. 11*:2067-2070, Elsevier Science Ltd., England (2001).

Seko, T., et al., "Structure-Activity Study of L-Amino Acid-Based N-Type Calcium Channel Blockers," *Bioorg. Med. Chem. 11*:1901-1913, Elsevier Science Ltd., England (2003).

Seko, T., et al., "Structure-Activity Study of L-Cysteine-Based N-Type Calcium Channel Blockers: Optimization of N- and C-Terminal Substituents," *Bioorg. Med. Chem. Lett. 12*:915-918, Elsevier Science Ltd., England (2002).

Sindelar, K., et al., "Neurotropic and Psychotropic Agents. LXVII. 1-[4,4-Bis(4-Fluorophenyl)Butyl]-4-Hydroxy-4-(3-Trifluoro-Methyl-4-Chlorophenyl)Piperidine and Related Compounds: New Synthetic Approaches," *Collect. Czeckoslov. Chem. Commun. 38*:3879-3901, Nakladatelstvi Ceskoslovenski Akademie Ved, Czech Republic (1973).

Song, Y., et al., "(S)-4-Methyl-2-(methylamino)pentanoic Acid [4,4-Bis(4-fluorophenyl)butyl]amide Hydrochloride, a Novel Calcium Channel Antagonist, Is Efficacious in Several Animal Models of Pain," *J. Med. Chem. 43*:3474-3477, American Chemical Society, United States (2000).

Stein, C., et al., "Unilateral Inflammation of the Hindpaw in Rats as a Model of Prolonged Noxious Stimulation: Alterations in Behavior and Nociceptive Thresholds," *Pharmacol. Biochem. Behav. 31*:445-451, Pergamon Press plc., United States (1988).

Takahara, A., et al., "Neuronal $Ca^{2+}$ Channel Blocking Action of an Antihypertensive Drug, Cilnidipine, in IMR-32 Human Neuroblastoma Cells," *Hypertens Res. 26*:743-747, Research Publishing House, England (2003).

Teodori, E., et al., "Design, Synthesis, and Preliminary Pharmacological Evaluation of 4-Aminopiperidine Derivatives as N-Type Calcium Channel Blockers Active on Pain and Neuropathic Pain," *J. Med. Chem. 47*:6070-6081, American Chemical Society, United States (2004).

Tomiyama, H., et al., "Cilnidipine More Highly Attenuates Cold Pressor Stress-Induced Platelet Activation in Hypertension than Does Amlodipine," *Hypertens. Res. 24*:679-684, The Society, England (2001).

Tsien, R.Y., "New Calcium Indicators and Buffers with High Selectivity against Magnesium and Protons: Design, Synthesis, and Properties of Prototype Structures," *Biochemistry 19*:2396-2404, American Chemical Society, United States (1980).

van de Waterbeemd, H., et al., "Property-Based Design: Optimization of Drug Absorption and Pharmacokinetics," *J. Med. Chem.* 44:1313-1333, American Chemical Society, United States (2001).

van Tonder, E.C., et al., "Preparation and Physicochemical Characterization of 5 Niclosamide Solvates and 1 Hemisolvate," *AAPS PharmSciTech* 5:Article 12, American Association of Pharmaceutical Scientists, United States (2004).

Vanegas, H. and Schaible, H.-G., "Effects of antagonists to high-threshold calcium channels upon spinal mechanisms of pain, hyperalgesia and allodynia," *Pain* 85:9-18, Elsevier Science B.V., Netherlands (2000).

Vasudevan, A., et al., "Identification of aminopiperidine benzamides as MCHr1 antagonists," *Bioorg. Med. Chem. Letts.* 15:3412-3416, Elsevier Ltd., England (2005).

Vippagunta, S.R., et al., "Crystalline solids," *Adv. Drug Deliv. Rev.* 48:3-26, Elsevier Science B.V., Netherlands (2001).

Wallace, M.S., "Calcium and Sodium Channel Antagonists for the Treatment of Pain," *Clin. J. Pain* 16:S80-S85, Lippincott Williams & Wilkins, Inc., United States (2000).

West, A.R., *Solid State Chemistry and its Applications*, John Wiley & Sons, United States, p. 358 & 365 (1988).

Williams, J.A., et al., "Ziconotide: an update and review," *Expert Opin. Pharmacother.* 9:1575-1583, Informa UK Ltd, United Kingdom (Jun. 2008).

Wolff, M.E., ed., *Burger's Medicinal Chemistry and Drug Discovery, Fifth Edition. vol. I: Principles and Practice*, p. 975-977, John Wiley & Sons, Inc., United States, (1995).

Wu, C.-F., et al., "Dissociated Neurons From Normal and Mutant *Drosophia* Larval Central Nervous System In Cell Culture," *J. Neurosci.* 3:1888-1899, Society of Neuroscience, United States (1983).

Wu, K.-M. and Farrelly, J.G., "Regulatory perspectives of Type II prodrug development and time-dependent toxicity management: Nonclinical Pharm/Tox analysis and the role of comparative toxicology," *Toxicology* 236:1-6, Elsevier Ireland Ltd., Ireland (Apr. 2007).

Xia, M., et al., "State-dependent inhibition of L-type calcium channels: cell-based assay in high-throughput format," *Anal. Biochem.* 327:74-81, Elsevier Inc., United States (2004).

Yamamoto, T., et al., "Discovery, structure-activity relationship study, and oral analgesic efficacy of cyproheptadine derivatives possessing N-type calcium channel inhibitory activity," *Bioorg. Med. Chem.* 14:5333-5339, Elsevier Ltd., England (Apr. 2006).

Youngman, M.A., et al., "α-Substituted N-(Sulfonamido)alkyl-β-aminotetralins: Potent and Selective Neuropeptide Y Y5 Receptor Antagonists," *J. Med. Chem.* 43:346-350, American Chemical Society, United States (2000).

Dialog File 351, Accession No. 15133660, Derwent WPI English language abstract for JP 2005/179351 A, accessed Jun. 30, 2008.

English language Abstract of Japanese Patent Publication No. JP 5-201971 A, European Patent Office, espacenet database—Worldwide (2001).

English language Abstract of International Patent Publication No. WO 2004/083167 A1, European Patent Office, espacenet database—Worldwide (2004).

English language Abstract of Japanese Patent Publication No. JP 2006-83133 A, European Patent Office, espacenet database—Worldwide (Mar. 2006).

English language Abstract of Japanese Patent Publication No. JP 2006-83137 A, European Patent Office, espacenet database—Worldwide (Mar. 2006).

English language Abstract of International Patent Publication No. WO 2007/052843 A1, European Patent Office, espacenet database—Worldwide (May 2007).

File Chemcats, Accession No. 2004:992362 CHEMCATS, Chemical Name: N-[1-(2,6-Dimethoxybenzyl)piperidin-4-yl]-N-propyl-3-(trifluoromethyl)benzenesulfonamide, published May 3, 2004 (XP002375662).

File Chemcats, Accession No. 2004:992806 CHEMCATS, Chemical Name: N-Cyclopropyl-N-(1-propylpiperidin-4-yl)-3-(trifluoromethyl)benzenesulfonamide, published May 3, 2004 (XP002375661).

File Chemcats, Accession No. 2004:992813 CHEMCATS, Chemical Name: N-(1-Benzylpiperidin-4-yl)-N-(cyclopropyl)benzenesulfonamide, published May 3, 2004 (XP002375665).

File Chemcats, Accession No. 2004:992822 CHEMCATS, Chemical Name: N-(1-Acetylpiperidin-4-yl)-4-chloro-N-(cyclopropyl)benzenesulfonamide, published May 3, 2004 (XP002375664).

File Chemcats, Accession No. 2013992854 CHEMCATS, Chemical Name: 1-(2-Chlorobenzoyl)-4-[cyclopropyl (phenylsulfonyl) amino] piperidine, published May 3, 2004 (XP002450197).

File Registry, Registration No. 680874-24-2 ZREGISTRY, Chemical Name: Benzenesulfonamide, N-[(4-ethoxyphenyl)methyl]-N-[1-(phenylmethyl)-4-piperidinyl]-3-(trifluoromethyl), dated May 9, 2004 (XP002375663).

File Chemcats, Accession No. 2019241436 CHEMCATS, Chemical Name: 4-(Cyclopropyl (phenylsulfonyl) amino)-1-[(1-(5-(trifluoromethyl) pyridin-2-yl)piperidin-4-yl)carbonyl]piperidine, published Sep. 13, 2006 (XP002450198).

International Search Report for International Application No. PCT/EP2005/011105, European Patent Office, Netherlands, mailed on Sep. 7, 2006.

International Preliminary Report on Patentability and Written Opinion of the International Searching Authority for International Application No. PCT/EP2005/011105, The International Bureau of WIPO, Geneva, Switzerland, issued on Apr. 17, 2007.

International Search Report for International Patent Application No. PCT/EP2007/053053, European Patent Office, Rijswijk, Netherlands, mailed on Jul. 19, 2007.

International Search Report for International Patent Application No. PCT/EP2007/053620, European Patent Office, Rijswijk, Netherlands, mailed on Aug. 7, 2007.

International Search Report for International Application No. PCT/EP2007/053622, European Patent Office, Rijswijk, Netherlands, mailed on Oct. 1, 2007.

International Preliminary Report on Patentability and Written Opinion of the International Searching Authority for International Application No. PCT/EP2007/053053, European Patent Office, Rijswijk, Netherlands, issued on Jun. 20, 2008.

International Search Report for International Application No. PCT/US2008/004490, European Patent Office, Rijswijk, Netherlands, mailed on Aug. 5, 2008.

International Preliminary Report on Patentability and Written Opinion of the International Searching Authority for International Application No. PCT/EP2007/053620, The International Bureau of WIPO, Geneva, Switzerland, issued on Oct. 14, 2008.

International Preliminary Report on Patentability and Written Opinion of the International Searching Authority for International Application No. PCT/EP2007/053622, The International Bureau of WIPO, Geneva, Switzerland, issued on Oct. 14, 2008.

International Search Report for International Patent Application No. PCT/IB2008/002575, European Patent Office, Rijswijk, Netherlands, mailed on Sep. 29, 2009.

International Preliminary Report on Patentability and Written Opinion of the International Searching Authority for International Application No. PCT/US2008/004490, The International Bureau of WIPO, Geneva, Switzerland, issued on Oct. 13, 2009.

International Preliminary Report on Patentability and Written Opinion of the International Searching Authority for International Application No. PCT/IB2008/002575, The International Bureau of WIPO, Geneva, Switzerland, issued on Mar. 30, 2010.

Office Action mailed Jul. 16, 2010 in U.S. Appl. No. 12/296,799, Chen et al., having a 35 U.S.C. § 371 (c) date of Jan. 30, 2009.

Office Action mailed Jun. 22, 2011, in U.S. Appl. No. 11/665,345, Benjamin et al., having a 35 U.S.C. § 371 (c) date of Nov. 17, 2008.

Office Action mailed Aug. 23, 2011, in U.S. Appl. No. 12/225,743, Chen et al., having a 35 U.S.C. § 371 (c) date of Mar. 26, 2009.

Office Action mailed Mar. 29, 2011 in U.S. Appl. No. 12/296,799, Chen et al., having a 35 U.S.C. § 371 (c) date of Jan. 30, 2009.

Office Action mailed Mar. 30, 2011, in U.S. Appl. No. 12/296,788, Matsumura et al., having a 35 U.S.C. § 371 (c) date of Oct. 10, 2008.

Office Action mailed Dec. 13, 2011, in U.S. Appl. No. 12/225,743, Chen et al., having a 35 U.S.C. § 371 (c) date of Mar. 26, 2009.

Office Action mailed Jan. 3, 2012, in U.S. Appl. No. 12/296,788, Matsumura et al., having a 35 U.S.C. § 371 (c) date of Oct. 10, 2008.
STNEasy Database, Accession No. 2007:510466, English language abstract for Miura, S., et al., "Preparation of heterocyclic amide compounds as FXR inhibitors," WIPO Patent Publication WO 2007/052843 A1 (XP002444167) (May 2007).
Unverified English language abstract for Japanese Patent Publication No. JP 2005/154380 A, espacenet Database, European Patent Office (2005).
McGivern, J.G., "Ziconotide: a review of its pharmacology and use in the treatment of pain," *Neuropsychiatric Disease and Treatment* 3(1):69-85, Dove Medical Press Limited, United States (Feb. 2007).
Melemeni, A., et al., "Gabapentin for acute and chronic post-surgical pain," *Signa Vitae 2 Suppl 1*:42-51, Pharmamed Mado Ltd., Croatia (May 2007).

Montazeri, K., et al., "Pre-emptive gabapentin significantly reduces postoperative pain and morphine demand following lower extremity orthopaedic surgery," *Singapore Med. J., 48*(8):748-751, Singapore Medical Assn., Singapore (Aug. 2007).
Office Action mailed Jul. 12, 2012, in U.S. Appl. No. 12/599,608, Shao et al., having a 35 U.S.C § 371 (c) date of Nov. 10, 2009.
Notice of Allowance mailed Mar. 30, 2012, in U.S. Appl. No. 12/225,743, Chen et al., having a 35 U.S.C. § 371 (c) date of Mar. 26, 2009.
Office Action mailed Feb. 24, 2012 in U.S. Appl. No. 11/665,345, Benjamin et al., having a 35 U.S.C. § 371 (c) date of Nov. 17, 2008.

* cited by examiner

BENZENESULFONYL COMPOUNDS AND THE USE THEREOF

This application is a National Stage of International Application No. PCT/EP2008/004490, filed Apr. 8, 2008, which claims the benefit of U.S. Provisional Application No. 60/907,571, filed Apr. 9, 2007.

REFERENCE TO SEQUENCE LISTING SUBMITTED ELECTRONICALLY

The content of the electronically submitted Sequence Listing; file name 1861_2300002_SequenceListing_ascii.txt; 2,615 bytes; and date of creation Jan. 9, 2013, filed herewith, is incorporated herein by reference in its entirety.

A Sequence Listing is submitted electronically in ASCII text file as part of an associated file. Please insert the Sequence Listing after the Claims.

BACKGROUND OF THE INVENTION

1. Field of the Invention

This invention is in the field of medicinal chemistry. The invention relates to novel pyrrolidinyl, piperidinyl, and hexahydroazepinyl compounds and the use of these compounds as blockers of calcium ($Ca^{2+}$) channels.

2. Background Art

Calcium ions play fundamental roles in the regulation of many cellular processes. It is therefore essential that their intracellular levels be maintained under strict, yet dynamic control (Davila, H. M., *Annals of the New York Academy of Sciences*, pp. 102-117 (1999)). Voltage-gated calcium channels (VGCC) serve as one of the important mechanisms for fast calcium influx into the cell. Calcium channels are hetero-oligomeric proteins consisting of a pore-forming subunit ($\alpha$1), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) voltage-activated R-type channels; and (iii) low voltage-activated (LVA) T-type channels (Davila, supra). Voltage-gated calcium channels (VGCC) are also known as voltage-dependent calcium channels (VDCC) or voltage-sensitive calcium channels (VSCC).

Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (Hu et al., *Bioorganic & Medicinal Chemistry* 8:1203-1212 (2000)). N-type channels are found mainly in central and peripheral neurons, being primarily located on presynaptic nerve terminals. These channels regulate the calcium flux required for depolarization-evoked release of a transmitter from synaptic endings. The transmission of pain signals from the periphery to the central nervous system (CNS) is mediated by N-type calcium channels located in the spinal cord (Song et al., *J. Med. Chem.* 43:3474-3477 (2000)).

The six types of calcium channels (i.e., L, N, P, Q, R, and T) are expressed throughout the nervous system (Wallace, M. S., *The Clinical Journal of Pain* 16:580-585 (2000)). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (supra) suggests that based on animal models, N-type calcium channel antagonists have a greater analgesic potency than sodium channel antagonists.

N-type calcium channel blockers have usefulness for neuroprotection and analgesia. Ziconotide, which is a selective N-type calcium channel blocker, has been found to have analgesic activity in animal models and neuroprotective activity in focal and global ischemia models (Song et al., supra). Examples of known calcium channel blockers include flunarizine, fluspirilene, cilnipide, PD 157767, SB-201823, SB-206284, NNC09-0026, and PD 151307 (Hu et al., supra).

Blockade of N-type channels can prevent and/or attenuate subjective pain as well as primary and/or secondary hyperalgesia and allodynia in a variety of experimental and clinical conditions (Vanegas, H. et al., *Pain* 85:9-18 (2000)). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (Song et al., supra). However, inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

BRIEF SUMMARY OF THE INVENTION

The present invention is related to the use of pyrrolidinyl, piperidinyl, and hexahydroazepinyl compounds represented by Formula I, below, and the pharmaceutically acceptable salts, prodrugs and solvates thereof, as blockers of calcium ($Ca^{2+}$) channels. Compounds of Formula I show selectivity as N-type calcium channel blockers.

The invention is also related to treating a disorder responsive to the blockade of calcium channels in a mammal suffering from excess activity of said channels by administering an effective amount of a compound of Formula I, or a pharmaceutically acceptable salt, prodrug or solvate thereof, as described herein. Specifically, the invention is related to treating a disorder responsive to the blockade of N-type calcium channels in a mammal suffering from excess activity of said channels by administering an effective amount of a compound of Formula I, or a pharmaceutically acceptable salt, prodrug or solvate thereof, as described herein.

Compounds useful in the present invention have not been heretofore reported. Thus, one aspect of the present invention is directed to novel compounds of Formula I, as well as their pharmaceutically acceptable salts, prodrugs and solvates.

Another aspect of the present invention is directed to the use of the novel compounds of Formula I, and their pharmaceutically acceptable salts, prodrugs and solvates, as blockers of N-type calcium channels.

A further aspect of the present invention is to provide a method for treating pain (e.g., acute pain, chronic pain, which includes but is not limited to, neuropathic pain and inflammatory pain, or surgical pain) by administering an effective amount of a compound of Formula I, or a pharmaceutically acceptable salt, prodrug or solvate thereof, to a mammal in need of such treatment. Specifically, the present invention provides a method for preemptive or palliative treatment of pain by administering an effective amount of a compound of Formula I, or a pharmaceutically acceptable salt, prodrug or solvate thereof, to a mammal in need of such treatment.

A further aspect of the present invention is to provide a method for treating stroke, neuronal damage resulting from head trauma, epilepsy, migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, by administering an effective amount of a compound of Formula I, or a pharmaceutically acceptable salt, prodrug or solvate thereof, to a mammal in need of such treatment.

A further aspect of the present invention is to provide a pharmaceutical composition useful for treating a disorder responsive to the blockade of calcium ion channels, especially N-type calcium ion channels, said pharmaceutical composition containing an effective amount of a compound of Formula I, or a pharmaceutically acceptable salt, prodrug or solvate thereof, in a mixture with one or more pharmaceutically acceptable carriers.

Also, an aspect of the invention is to provide a method of modulating calcium channels, especially N-type calcium channels, in a mammal, wherein said method comprises administering to the mammal an effective amount of at least one compound of Formula I, or a pharmaceutically acceptable salt, prodrug or solvate thereof.

A further aspect of the present invention is to provide radiolabeled compounds of Formula I and the use of such compounds, or their pharmaceutically acceptable salts, prodrugs or solvates, as radioligands for their binding site on the calcium channel.

A further aspect of the invention is to provide a method for screening a candidate compound for the ability to bind to a receptor using a radiolabeled compound of Formula I, which includes but is not limited to, a $^3$H, and $^{14}$C radiolabeled compound of Formula I, or a pharmaceutically acceptable salt, prodrug or solvate thereof. This method comprises a) introducing a fixed concentration of the radiolabeled compound to the receptor to form a mixture; b) titrating the mixture with a candidate compound; and c) determining the binding of the candidate compound to said receptor.

A further aspect of the invention is to provide the use of a compound of Formula I, or a pharmaceutically acceptable salt, prodrug or solvate thereof, in the manufacture of a medicament for treating pain in a mammal. In one embodiment, the invention provides the use of a compound of Formula I, or a pharmaceutically acceptable salt, prodrug or solvate thereof, in the manufacture of a medicament for palliative or premptive treatment of pain, such as acute pain, chronic pain, or surgical pain.

A further aspect of the invention is to provide the use of a compound of Formula I, or a pharmaceutically acceptable salt, prodrug or solvate thereof, in the manufacture of a medicament for treating stroke, neuronal damage resulting from head trauma, epilepsy, migraine, a mood disorder, schizophrenia, a neurodegenerative disorder, depression, anxiety, a psychosis, hypertension, or cardiac arrhythmia in a mammal.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DETAILED DESCRIPTION OF THE INVENTION

One aspect of the present invention is based on the use of compounds of Formula I, and the pharmaceutically acceptable salts, prodrugs and solvates thereof, as blockers of $Ca^{2+}$ channels. In view of this property, compounds of Formula I, and the pharmaceutically acceptable salts, prodrugs and solvates thereof, are useful for treating disorders responsive to the blockade of calcium ion channels. In one aspect, compounds of Formula I, and the pharmaceutically acceptable salts, prodrugs and solvates thereof, selectively block N-type calcium ion channels and, thus, are useful for treating disorders responsive to the selective blockade of N-type calcium ion channels.

The compounds useful in this aspect of the invention are compounds represented by Formula I:

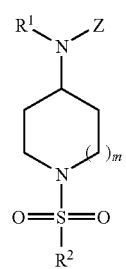

and pharmaceutically acceptable salts, prodrugs and solvates thereof, wherein:

$R^1$ is selected from the group consisting of hydrogen, $C_1$-$C_6$ alkyl, $C_2$-$C_6$ alkenyl, halo($C_1$-$C_6$)alkyl, $C_1$-$C_6$ alkoxy($C_1$-$C_6$)alkyl, halo($C_1$-$C_6$)alkoxy($C_1$-$C_6$)alkyl, hydroxy($C_1$-$C_6$)alkyl, amino($C_1$-$C_6$)alkyl, $C_1$-$C_6$ alkylamino($C_1$-$C_6$)alkyl, di($C_1$-$C_6$)alkylamino($C_1$-$C_6$)alkyl, cycloalkyl, and heterocyclo($C_1$-$C_6$)alkyl, all of which can be optionally substituted;

$R^2$ is selected from the group consisting of $C_1$-$C_6$ alkyl, cycloalkyl, optionally substituted aryl, optionally substituted heteroaryl, and di($C_1$-$C_6$)alkylamino;

Z is selected from the group consisting of $Z^1$, $Z^2$, and $Z^3$ wherein:

$Z^1$ is

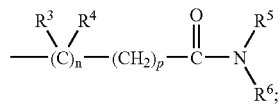

$Z^2$ is

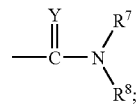

and $Z^3$ is

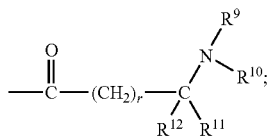

m is 0, 1, or 2;
n is 0, 1 or 2;
p is 0 or 1; provided that n and p are not both 0;
r is 0 or 1,
$R^3$ and $R^4$ are each independently hydrogen, alkyl, or alkenyl; or
$R^3$ and $R^4$ together form =O; or
$R^3$ and $R^4$ together with the carbon atom to which they are attached form a saturated $C_{3-7}$ cycloalkyl ring optionally substituted with one substituent selected from the group consisting of alkyl, hydroxy, hydroxyalkyl, amino, and =O, wherein one or more carbon atoms of the $C_{3-7}$ cycloalkyl ring are optionally replaced with $NR^{16}$, O, S, or $SO_2$, wherein $R^{16}$ is hydrogen or $C_{1-3}$ alkyl, to form a heterocyclic ring;
$R^5$ is selected from the group consisting of alkyl, optionally substituted aryl, optionally substituted arylalkyl, and optionally substituted heteroaryl;
$R^6$ is selected from the group consisting of hydrogen, alkyl, alkenyl, optionally substituted cycloalkyl, optionally substituted aryl, optionally substituted arylalkyl, and optionally substituted heteroaryl; or
$R^5$ and $R^6$ together with the nitrogen atom to which they are attached form a heterocyclic ring to give $Z^{11}$ having the structure:

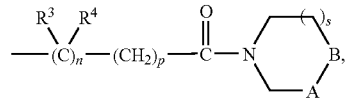

where
A is $CH_2$, CHF, $CF_2$ or CHOH;
B is $CH_2$, O, or $N-R^{51}$, where $R^{51}$ is $CH_3$ or $C(O)CH_3$;
s is 0, 1, or 2;
p is 0 or 1;
$R^3$ is as defined above and $R^4$ is hydrogen; or
$R^7$ is selected from the group consisting of alkyl, optionally substituted heterocyclo, optionally substituted aryl, optionally substituted arylalkyl, optionally substituted heteroaryl, optionally substituted heteroarylalkyl, and $-CH_2-U-V$, wherein U is $CH_2$, CHF, $CF_2$ or CHOH and V is hydrogen, alkyl, or alkenyl;
$R^8$ is selected from the group consisting of hydrogen, alkyl, alkenyl, optionally substituted cycloalkyl, optionally substituted aryl, optionally substituted arylalkyl, optionally substituted heteroaryl, and optionally substituted heteroarylalkyl;
(i) $R^9$ and $R^{10}$ are each independently selected from the group consisting of
hydrogen;
alkyl;
alkenyl;
hydroxyalkyl;
alkoxyalkyl;
cycloalkyl, and
phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; or
$R^9$ is hydrogen, alkyl, alkenyl, hydroxyalkyl, alkoxyalkyl, cycloalkyl, or phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; and
$R^{10}$ is $R^{17}-C(O)-$, where
$R^{17}$ is selected from the group consisting of alkyl, alkoxy, optionally substituted benzyl, and optionally substituted benzyloxy; or
$R^9$ and $R^{10}$ together with the nitrogen atom to which they are attached form a 5- or 6-membered heterocyclic ring wherein one or more carbon atoms of the heterocyclic ring are optionally replaced with $NR^{18}$, O, or S, wherein $R^{18}$ is hydrogen or $C_{1-3}$ alkyl;
$R^{11}$ and $R^{12}$ are each independently selected from the group consisting of
hydrogen;
alkyl;
alkenyl;
hydroxyalkyl;
aminoalkyl;
cycloalkyl;
heterocyclo;
heterocycloalkyl;
phenyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyloxyalkyl;
heteroaryl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; and
heteroarylalkyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; or
$R^{11}$ and $R^{12}$ together form =O; or
$R^{11}$ and $R^{12}$ together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or wherein two adjacent carbon atoms of the $C_{3-7}$ cycloalkyl ring can form a bridge —O— to form a bicyclic ring; or wherein two adjacent carbon atoms of the $C_{3-7}$ cycloalkyl ring together form a fused phenyl group optionally substituted with alkyl, haloalkyl, amino, cyano, or hydroxy; or
$R^{12}$ is hydrogen, alkyl, or alkenyl; $R^9$ is as defined above; and $R^{10}$ and $R^{11}$ together form a bridge $-CH_2-CH_2-CH_2-$ or $-CH_2-CHG^1-CHG^2-CH_2-$, wherein $G^1$ and $G^2$ are both hydrogen or together with the carbon atoms to which they are attached form a fused phenyl group; or (ii) $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ is selected from the group consisting of hydrogen, alkyl, alkenyl, optionally substituted cycloalkyl, optionally substituted aryl, optionally substituted arylalkyl, optionally substituted heteroaryl, and optionally substituted heteroarylalkyl; or $R^9$ and $R^{10}$ together with the nitrogen atom to which they are attached form a heterocyclic ring to give $Z^{31}$ having the structure:

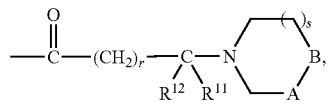

where

A is $CH_2$, CHF, $CF_2$ or CHOH;
B is $CH_2$, O, or N—$R^{51}$, where $R^{51}$ is $CH_3$ or $C(O)CH_3$; and
s is 0, 1, or 2;
r is 0 or 1; and
$R^{11}$ and $R^{12}$ together form =O; or
$R^{11}$ and $R^{12}$ are each independently selected from the group consisting of hydrogen, alkyl, and alkenyl or together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or (iii) $R^{11}$ and $R^{12}$ are both hydrogen or together form =O; $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ and $R^1$ together form a bridge -D-E-G-, wherein D is $CH_2$, C(O), $CHCH_3$, $C(CH_3)_2$ or absent;
E is $CH_2$, C(O), C(S), CHF, $CF_2$ or CHOH; and
G is $CH_2$, C(O), $CHCH_3$, $C(CH_3)_2$ or absent; and
Y is O or S.

The carbon of the pyrrolidinyl, piperidinyl, and hexahydroazepinyl ring where the Z group is attached, can be a chiral center. Accordingly, the configuration at those carbon atoms can be (R) or (S).

One group of compounds useful in this aspect of the present invention are compounds of Formula I as defined above, with the following provisos:

1) $R^7$ is not optionally substituted 2-thiazolyl or optionally substituted benzothiazolyl;

2) when Z is $Z^2$, then $R^2$ is not $C_{1-6}$ alkyl, cycloalkyl or unsubstituted phenyl;

3) when Z is $Z^2$, $R^8$ is hydrogen or alkyl, and $R^7$ is an optionally substituted phenyl or biphenyl, then $R^1$ is other than hydrogen or unsubstituted alkyl;

4) when Z is $Z^3$ and m is 2, then $R^2$ is not phenyl substituted with CN or $R^9$ and $R^{10}$ are not both hydrogen;

5) when Z is $Z^3$ and $R^9$ and $R^{10}$ are both hydrogen, then $R^1$ is other than hydrogen; or 6) when Z is $Z^3$, r is 0, and $R^{11}$ and $R^{12}$ are both hydrogen, then $R^1$ is other than unsubstituted $C_{1-6}$ alkyl.

In one embodiment, compounds useful in the present invention are compounds represented by Formula II:

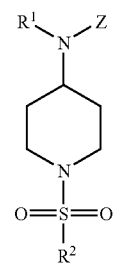

II and pharmaceutically acceptable salts, prodrugs, and solvates thereof, wherein $R^1$, $R^2$, and Z are as defined above.

In one embodiment, compounds useful in the present invention are compounds represented by Formula III:

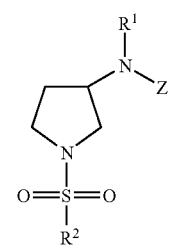

III and pharmaceutically acceptable salts, prodrugs, and solvates thereof, wherein $R^1$, $R^2$, and Z are as defined above.

In one embodiment, compounds useful in the present invention are compounds represented by Formula IV:

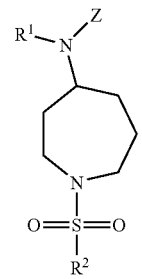

IV and pharmaceutically acceptable salts, prodrugs, and solvates thereof, wherein $R^1$, $R^2$, and Z are as defined above.

In one embodiment, compounds useful in the present invention are compounds of any of Formulae I-IV where Z is $Z^1$.

In one aspect, useful compounds falling into the scope of any of Formulae I-IV are those where Z is $Z^{11}$ having the structure:

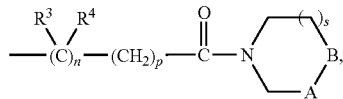

where $R^3$, $R^4$, A, B, n, p, and s are as defined above.

In one aspect, useful compounds falling within the scope of any of Formulae I-IV are those where Z is $Z^{12}$ having the structure:

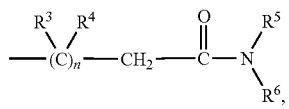

wherein $R^3$-$R^6$ and n are as defined above.

In one embodiment, compounds useful in the present invention are compounds of any of Formulae I-IV, wherein Z is $Z^1$ and p is 0.

In one embodiment, compounds useful in the present invention are compounds of any of Formulae I-IV, wherein Z is $Z^1$ and p is 1.

In one embodiment, compounds useful in the present invention are compounds of any of Formulae I-IV, wherein Z is $Z^1$ and $R^3$ and $R^4$ are each independently hydrogen, alkyl, or alkenyl.

In one embodiment, compounds useful in the present invention are compounds of any of Formulae I-IV, wherein Z is $Z^1$ and $R^3$ and $R^4$ together form =O.

In one embodiment, compounds useful in the present invention are compounds of any of Formulae I-IV, wherein Z is $Z^1$ and $R^3$ and $R^4$ together with the carbon atom to which they are attached form a saturated $C_{3-7}$ cycloalkyl ring optionally substituted with one substituent selected from the group consisting of alkyl, hydroxy, hydroxyalkyl, amino, and =O, wherein one or more carbon atoms of the $C_{3-7}$ cycloalkyl ring are optionally replaced with $NR^{16}$, O, S, or $SO_2$, wherein $R^{16}$ is hydrogen or $C_{1-3}$ alkyl, to form a heterocyclic ring. Useful compounds include those where $R^3$ and $R^4$ together form a $C_{3-6}$ carbocyclic ring. Further useful compounds include those where $Z^1$ is $Z^{13}$ having the structure:

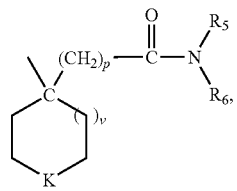

where $R^5$, $R^6$, and p are as defined above, K is selected from the group consisting of $CH_2$, O, S, $SO_2$, and $NR^{16}$, and v is 0, 1, or 2.

Preferably, $Z^1$ is selected from the group consisting of $Z^{14}$, $Z^{15}$ and $Z^{16}$, wherein:
$Z^{14}$ is

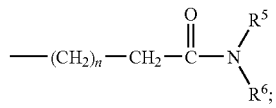

$Z^{15}$ is

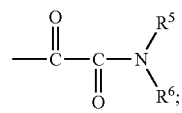

and
$Z^{16}$ is

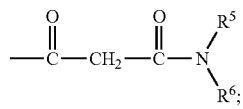

wherein $R^5$, $R^6$ and n are as defined above. Preferably, $R^6$ is hydrogen and n is 0 or 1. More preferably, $R^5$ is optionally substituted $C_{6-10}$ aryl or optionally substituted heteroaryl having 5-10 ring atoms. Useful compounds of any of Formulae I-IV include those where $R^5$ is selected from the group consisting of phenyl, naphthyl, indenyl, isoindenyl, pyridyl, pyrimidinyl, pyrazinyl, pyridazinyl, triazinyl, pyrrolyl, pyrazolyl, benzothiazolyl, thiazolyl, imidazolyl, benzoimidazolyl, benzoxazolyl, indolyl, indazolyl, and benzotriazolyl, all of which can be optionally substituted. Preferably, $R^5$ is optionally substituted phenyl or pyridyl. More preferably, $R^5$ is phenyl or pyridyl that is unsubstituted or substituted with one or two substituents each independently selected from the group consisting of alkyl, haloalkyl, halogen, hydroxy, hydroxyalkyl, alkoxy, and cyano.

Useful compounds of any of Formulae I-IV include those where $Z^1$ is selected from the group consisting of $Z^{17}$ and $Z^{18}$, wherein
$Z^{17}$ is

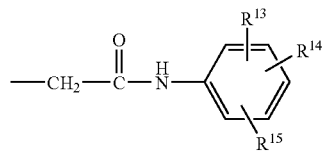

and
$Z^{18}$ is

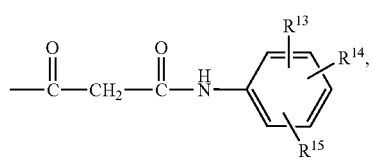

wherein $R^{13}$, $R^{14}$ and $R^{15}$ are each independently selected from the group consisting of hydrogen, alkyl, alkoxy, halogen, haloalkyl, hydroxy, hydroxyalkyl, cyano, amino, aminoalkyl, alkylamino, dialkylamino, hydroxyalkylamino, —C(O)OR$^{20}$, and —C(O)NR$^{20}$R$^{21}$, wherein $R^{20}$ and $R^{21}$ are each independently selected from the group consisting of hydrogen, alkyl, alkenyl, optionally substituted heterocyclo, optionally substituted cycloalkyl, optionally substituted aryl, optionally substituted arylalkyl, optionally substituted heteroaryl, optionally substituted heteroarylalkyl, and —CH$_2$—U—V, wherein U is CH$_2$, CHF, CF$_2$ or CHOH and V is hydrogen, alkyl, alkenyl or aryl.

The groups $R^{13}$, $R^{14}$, and $R^{15}$, when they are not equal to H, each take the place of a hydrogen atom that would otherwise be present in any position on the phenyl ring to which the particular R group is attached. Similarly, optional substituents attached to aryl, phenyl, and heteroaryl rings each take the place of a hydrogen atom that would otherwise be present in any position on the aryl or heteroaryl rings.

In one embodiment, compounds useful in the present invention are compounds of any of Formulae I-IV where Z is $Z^2$. A group of useful compounds include those where Y is O. Another group of useful compounds include those where Y is S.

In one aspect, useful compounds falling within the scope of any of Formulae I-IV are those where $Z^2$ is $Z^{21}$ having the structure:

wherein Y is O or S and $R^7$ is selected from the group consisting of aryl and heteroaryl, either of which can be optionally substituted. Preferably, $R^7$ is optionally substituted $C_{6-10}$ aryl or optionally substituted heteroaryl having 5-10 ring atoms. Useful compounds of any of Formulae I-IV include those where $R^7$ is selected from the group consisting of phenyl, naphthyl, indenyl, isoindenyl, pyridyl, pyrimidinyl, pyrazinyl, pyridazinyl, triazinyl, pyrrolyl, pyrazolyl, thiazolyl, imidazolyl, benzoimidazolyl, benzoxazolyl, indolyl, indazolyl, and benzotriazolyl all of which can be optionally substituted. Preferably, $R^7$ is optionally substituted phenyl or pyridyl.

In one embodiment, $R^7$ is unsubstituted phenyl or phenyl substituted with one, two, or three substituents each independently selected from the group consisting of alkyl, alkoxy, halogen, haloalkyl, hydroxy, hydroxyalkyl, cyano, amino, aminoalkyl, alkylamino, dialkylamino, and hydroxyalkylamino. In another embodiment, $R^7$ is pyridyl that is unsubstituted or substituted with one or two substituents each independently selected from the group consisting of alkyl, haloalkyl, halogen, hydroxy, hydroxyalkyl, alkoxy, and cyano.

In one embodiment, compounds useful in the present invention are compounds of any of Formulae I-IV where Z is $Z^3$.

In one embodiment, compounds useful in the present invention are compounds of any of Formulae I-IV, wherein Z is $Z^3$ and $R^9$ and $R^{10}$ are each independently selected from the group consisting of
hydrogen;
alkyl;
alkenyl;
hydroxyalkyl;
alkoxyalkyl;
cycloalkyl, and
phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy. Preferably, $R^9$ is hydrogen and $R^{10}$ is other than hydrogen.

In one embodiment, compounds useful in the present invention are compounds of any of Formulae I-IV, wherein Z is $Z^3$ and $R^9$ is hydrogen, alkyl, alkenyl, hydroxyalkyl, alkoxyalkyl, cycloalkyl, or phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; and
$R^{10}$ is $R^{17}$—C(O)—, where
$R^{17}$ is selected from the group consisting of alkyl, alkoxy, optionally substituted benzyl, and optionally substituted benzyloxy.

In one embodiment, compounds useful in the present invention are compounds of any of Formulae I-IV, wherein Z is $Z^3$ and $R^9$ and $R^{10}$ together with the nitrogen atom to which they are attached form a 5- or 6-membered heterocyclic ring wherein one or more carbon atoms of the heterocyclic ring are optionally replaced with NR$^{18}$, O, or S, wherein $R^{18}$ is hydrogen or $C_{1-3}$ alkyl.

In one embodiment, compounds useful in the present invention are compounds of any of Formulae I-IV, wherein Z is $Z^3$ and $R^{11}$ and $R^{12}$ are each independently selected from the group consisting of
hydrogen;
alkyl;
alkenyl;
hydroxyalkyl;
aminoalkyl;
cycloalkyl;
heterocyclo;
heterocycloalkyl;
phenyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyloxyalkyl;
heteroaryl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; and
heteroarylalkyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy.

In one embodiment, compounds useful in the present invention are compounds of any of Formulae I-IV, wherein Z is $Z^3$ and $R^{11}$ and $R^{12}$ together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or wherein two adjacent carbon atoms of the $C_{3-7}$ cycloalkyl ring can form a bridge —O— to form a bicyclic ring; or wherein two adjacent carbon atoms of the $C_{3-7}$ cycloalkyl ring together form a fused phenyl group optionally substituted with alkyl, haloalkyl, amino, cyano, or hydroxy.

In one embodiment, compounds useful in the present invention are compounds of any of Formulae I-IV, wherein Z is $Z^3$ and $R^{11}$ and $R^{12}$ together form =O.

In one embodiment, compounds useful in the present invention are compounds of any of Formulae I-IV, wherein Z is $Z^3$ and $R^{12}$ is hydrogen, alkyl, or alkenyl; $R^9$ is as defined above; and $R^{10}$ and $R^{11}$ together form a bridge —$CH_2$—$CH_2$—$CH_2$— or —$CH_2$—$CHG^1$-$CHG^2$-$CH_2$—, wherein $G^1$ and $G^2$ are both hydrogen or together with the carbon atoms to which they are attached form a fused phenyl group.

In one embodiment, useful compounds of Formulae I-IV include those where $R^9$ and $R^{10}$ are each independently selected from the group consisting of hydrogen, alkyl, hydroxyalkyl, and phenyl; more preferably independently selected from hydrogen, $C_{1-6}$ alkyl, hydroxy($C_{1-6}$)alkyl, and phenyl; more preferably independently selected from hydrogen, $C_{1-3}$ alkyl, hydroxy($C_{1-3}$)alkyl, and phenyl; and more preferably independently selected from hydrogen, methyl, ethyl, hydroxymethyl, hydroxyethyl, and phenyl; or $R^9$ and $R^{10}$ together with the nitrogen atom to which they are attached form a 5- or 6-membered heterocyclic ring selected from the group consisting of oxazolidinyl, isoxazolidinyl, pyrrolidinyl, pyrazolidinyl, imidazolidinyl, hexahydropyrimidinyl, piperidinyl, piperazinyl, 4-methylpiperazinyl, morpholinyl, thiomorpholinyl, and tetrahydropyridyl. Advantageously, $R^9$ and $R^{10}$ are independently hydrogen, methyl or hydroxyethyl, or $R^9$ and $R^{10}$ together with the nitrogen atom to which they are attached form 1-pyrrolidinyl, 4-thiomorpholinyl, piperazinyl, or 4-methylpiperazinyl.

In one embodiment, useful compounds of Formulae I-IV include those where $R^{11}$ is hydrogen and $R^{12}$ is selected from the group consisting of alkyl; hydroxyalkyl; cycloalkyl; heterocycloalkyl; phenyl optionally substituted with one or two substituents independently selected from the group consisting of alkyl, cycloalkyl, halogen, cyano, amino, alkylamino, dialkylamino, hydroxy, nitro, haloalkyl, and alkoxy; benzyl optionally substituted with one or two substituents independently selected from the group consisting of alkyl, cycloalkyl, halogen, cyano, amino, alkylamino, dialkylamino, hydroxy, nitro, haloalkyl, and alkoxy; and benzyloxyalkyl. More preferably, $R^{12}$ is selected from the group consisting of straight chain $C_{1-6}$ alkyl; branched chain $C_{3-6}$ alkyl; hydroxy($C_{1-6}$) alkyl; $C_{3-6}$ cycloalkyl; 5-7-membered heterocyclo($C_{1-4}$) alkyl; phenyl optionally substituted with one or two substituents independently selected from the group consisting of $C_{1-6}$ alkyl, $C_{3-6}$ cycloalkyl, halogen, cyano, amino, $C_{1-3}$ alkylamino, di($C_{1-3}$)alkylamino, hydroxy, nitro, halo($C_{1-6}$)alkyl, and $C_{1-6}$ alkoxy; benzyl optionally substituted with one or two substituents independently selected from the group consisting of $C_{1-6}$ alkyl, $C_{3-6}$ cycloalkyl, halogen, cyano, amino, $C_{1-3}$ alkylamino, di($C_{1-3}$)alkylamino, hydroxy, nitro, halo($C_{1-6}$)alkyl, and $C_{1-6}$ alkoxy; and benzyloxy($C_{1-3}$)alkyl. Advantageously, $R^{12}$ is methyl; propyl; iso-propyl; butyl; tert-butyl; sec-butyl; iso-butyl; hydroxymethyl; 1-hydroxyethyl; tetrahydropyran-4-ylmethyl; phenyl optionally substituted with one or two substituents independently selected from the group consisting of methyl ethyl, propyl, iso-propyl, butyl, tert-butyl, halogen, cyano, amino, methylamino, dimethylamino, hydroxy, nitro, and trifluoromethyl; benzyl optionally substituted with one or two substituents independently selected from the group consisting of methyl ethyl, propyl, iso-propyl, butyl, tert-butyl, halogen, cyano, amino, methylamino, dimethylamino, hydroxy, nitro, and trifluoromethyl; 1-benzyloxyethyl; cyclopentyl; cyclohexyl; cyclopentylmethyl; or cyclohexylmethyl.

Useful compounds include those where $R^{11}$ and $R^{12}$ together with the carbon atom to which they are attached form a $C_{3-6}$ cycloalkyl group, which is preferably cyclopentyl or cyclohexyl.

Useful compounds of any of Formulae I-IV include those where $R^9$ is hydrogen and $R^{10}$ is hydrogen, alkyl, hydroxyalkyl (e.g., 2-hydroxyethyl), or cycloalkyl (e.g., cyclohexyl); or $R^9$ and $R^{10}$ together with the nitrogen atom to which they are attached form a heterocyclic ring (e.g., 1-piperidinyl); $R^{11}$ is hydrogen, and $R^{12}$ is hydrogen, alkyl, cycloalkyl (e.g., cyclohexyl), heterocycloalkyl (e.g., 4-(2,3,5,6-tetrahydropyranyl)methyl), or benzyl optionally substituted with one or two substituents each independently selected from the group consisting of alkyl, haloalkyl, halogen, hydroxy, hydroxyalkyl, alkoxy and cyano.

In one embodiment, compounds useful in the present invention are compounds of any of Formulae I-IV, wherein Z is $Z^3$ and $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ is selected from the group consisting of hydrogen, alkyl, alkenyl, optionally substituted cycloalkyl, optionally substituted aryl, optionally substituted arylalkyl, optionally substituted heteroaryl, and optionally substituted heteroarylalkyl; or $R^9$ and $R^{10}$ together with the nitrogen atom to which they are attached form a heterocyclic ring to give $Z^{31}$ having the structure:

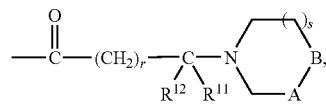

where

A is $CH_2$, CHF, $CF_2$ or CHOH;

B is $CH_2$, O, or N—$R^{51}$, where $R^{51}$ is $CH_3$ or $C(O)CH_3$; and s is 0, 1, or 2;

r is 0 or 1; and $R^{11}$ and $R^{12}$ together form =O; or $R^{11}$ and $R^{12}$ are each independently selected from the group consisting of hydrogen, alkyl, and alkenyl or together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring. In this embodiment, useful compounds include those where $R^{11}$ and $R^{12}$ together form a $C_{3-6}$ carbocyclic ring. Further useful compounds include those where $Z^3$ is $Z^{32}$ having the structure:

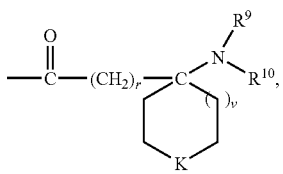

where $R^9$, $R^{10}$, and r are as defined above, K is selected from the group consisting of $CH_2$, O, S, $SO_2$, and $NR^{19}$, and v is 0, 1, or 2.

In one embodiment, compounds useful in the present invention are those where Z is $Z^3$, $R^{11}$ and $R^{12}$ are both hydrogen and $R^{10}$ and $R^1$ together form a bridge -D-E-G- represented by Formula V:

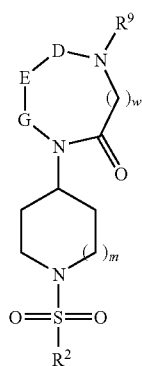

V where $R^2$, $R^9$, D, E, G, and m are as defined above and w is 1 or 2. Preferably, $R^9$ is optionally substituted $C_{6-10}$ aryl or optionally substituted heteroaryl having 5-10 ring atoms. Useful compounds of Formula V include those where $R^9$ selected from the group consisting of phenyl, naphthyl, indenyl, isoindenyl, pyridyl, pyrimidinyl, pyrazinyl, pyridazinyl, triazinyl, pyrrolyl, pyrazolyl, and benzothiazolyl, all of which can be optionally substituted. Preferably, $R^9$ is optionally substituted phenyl or pyridyl. In one embodiment, $R^9$ is unsubstituted phenyl or phenyl substituted with one, two, or three substituents each independently selected from the group consisting of alkyl, alkoxy, halogen, haloalkyl, hydroxy, hydroxyalkyl, cyano, amino, aminoalkyl, alkylamino, dialkylamino, and hydroxyalkylamino. In another embodiment, $R^9$ is pyridyl that is unsubstituted or substituted with one or two substituents each independently selected from the group consisting of alkyl, haloalkyl, halogen, hydroxy, hydroxyalkyl, alkoxy, and cyano.

Useful compounds of Formula V include those where m is 1. Further useful compounds of Formula V include those where w is 1. Preferable compounds of Formula V include those where m and w are both 1 and a) D is absent and E and G are both $CH_2$; or b) D, E and G are each $CH_2$.

In one embodiment, compounds useful in the present invention are those where Z is $Z^3$; $R^{11}$ and $R^{12}$ together form =O; $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ and $R^1$ together form a bridge -D-E-G-, wherein D is $CH_2$, C(O), $CHCH_3$, $C(CH_3)_2$ or absent; E is $CH_2$, C(O), C(S), CHF, $CF_2$, or CHOH; and G is $CH_2$, C(O), $CHCH_3$, $C(CH_3)_2$ or absent.

The present invention is also directed to compounds of Formula VI as follows:

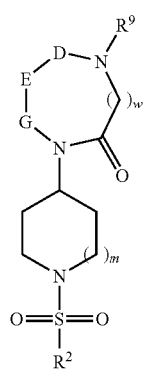

VI where $R^2$, $R^9$, D, E, G, and m are as defined above for Formula V and w is 0. Preferably, $R^2$, $R^9$, D, E, G and m as defined above for Formula V. One group of compounds useful in this aspect of the invention are compounds of Formula VI as defined above with the proviso that $R^2$ is not $C_{1-6}$ alkyl.

Preferably, in compounds of Formulae I-IV, $R^1$ is selected from the group consisting of hydrogen, $C_{1-6}$ alkyl, halo($C_{1-6}$)alkyl, $C_{1-4}$ alkoxy($C_{1-6}$)alkyl, halo($C_{1-4}$)alkoxy ($C_{1-6}$)alkyl, hydroxy($C_{1-6}$)alkyl, amino($C_{1-6}$)alkyl, $C_{1-4}$ alkylamino($C_{1-6}$)alkyl, di($C_{1-4}$)alkylamino($C_{1-6}$)alkyl, and $C_{3-7}$ cycloalkyl; and more preferably selected from the group consisting of hydrogen, $C_{1-6}$ alkyl, and $C_{3-7}$ cycloalkyl.

Preferably, in compounds of Formulae I-VI, $R^2$ is selected from the group consisting of
  a) cycloalkyl;
  b) aryl optionally substituted with one, two or three substituents each independently selected from the group consisting of alkyl, alkoxy, alkoxycarbonyl, cyano, halogen, haloalkyl, haloalkoxy, hydroxy, hydroxyalkyl, amino, alkylamino, dialkylamino, hydroxyalkylamino, —C(O)$OR^{20}$, and —C(O)$NR^{20}R^{21}$, wherein $R^{20}$ and $R^{21}$ are each independently selected from the group consisting of hydrogen, alkyl, alkenyl, optionally substituted heterocyclo, optionally substituted cycloalkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, alkenyl or aryl;
  c) heteroaryl optionally substituted with one, two or three substituents each independently selected from the group consisting of alkyl, alkoxy, hydroxy, hydroxyalkyl, cyano, amino, alkylamino, dialkylamino, hydroxyalkylamino, alkoxycarbonyl, carboxy, alkylcarbonylamino, alkylcarbonylaminoalkyl, halogen, haloalkyl, phenyl, phenoxy, heteroaryl, and heterocyclo; and
  d) di($C_{1-6}$)alkylamino.

More preferably, $R^2$ is phenyl or pyridyl unsubstituted or substituted with one or two substituents each independently selected from the group consisting of alkyl, alkoxy, halogen, haloalkyl, hydroxy, hydroxyalkyl, cyano, amino, alkylamino, dialkylamino and hydroxyalkylamino. In one embodiment, $R^2$ is phenyl substituted with alkyl, alkoxy, halogen, haloalkyl, hydroxy, hydroxyalkyl, cyano, amino, alkylamino, dialkylamino, hydroxyalkylamino, —C(O)$OR^{20}$, and —C(O)$NR^{20}R^{21}$, wherein $R^{20}$ and $R^{21}$ are each independently selected from the group consisting of hydrogen, alkyl, alkenyl, optionally substituted heterocyclo, optionally substituted cycloalkyl, optionally substituted aryl, optionally substituted arylalkyl, optionally substituted heteroaryl, optionally substituted heteroarylalkyl, and —CH$_2$—U—V, wherein U is CH$_2$, CHF, CF$_2$ or CHOH and V is hydrogen, alkyl, alkenyl or aryl; preferably substituted with C$_{1-4}$ alkyl, C$_{1-4}$ alkoxy, halo(C$_{1-4}$)alkyl, halogen, cyano, hydroxy, hydroxy(C$_{1-4}$)alkyl, carboxy, C$_{1-4}$ alkyloxycarbonyl, aminocarbonyl, C$_{1-4}$ alkylaminocarbonyl, or di(C$_{1-4}$)alkylaminocarbonyl; and more preferably substituted with haloalkyl, especially trifluoromethyl. Preferably, the substituent is in the meta-position of the phenyl ring. In one embodiment, R$^2$ is pyridyl unsubstituted or substituted with alkyl, alkoxy, halogen, haloalkyl, hydroxy, hydroxyalkyl, cyano, amino, alkylamino, dialkylamino or hydroxyalkylamino; preferably substituted with C$_{1-4}$ alkyl, C$_{1-4}$ alkoxy, halo(C$_{1-4}$)alkyl, halogen, cyano, hydroxy, hydroxy(C$_{1-4}$)alkyl; and more preferably substituted with haloalkyl, especially trifluoromethyl.

Useful alkyl groups for R$^2$ include straight chain or branched C$_{1-6}$ alkyl, preferably methyl, ethyl, n-propyl, isopropyl, n-butyl, sec-butyl, tert-butyl, n-pentyl, and 2-pentyl.

Useful cycloalkyl groups for R$^2$ include C$_{3-7}$ cycloalkyl groups, especially cyclopropyl, cyclopentyl, and cyclohexyl.

Useful aryl groups for R$^2$ include C$_{6-10}$ aryl groups optionally substituted with one, two or three substituents each independently selected from the group consisting of alkyl, alkoxy, alkoxycarbonyl, cyano, halogen, haloalkyl, haloalkoxy, hydroxy, hydroxyalkyl, amino, alkylamino, dialkylamino and hydroxyalkylamino; preferably phenyl or naphthyl optionally substituted with one, two or three substituents each independently selected from the group consisting of alkyl, alkoxy, alkoxycarbonyl, cyano, halogen, haloalkyl, haloalkoxy, hydroxy, hydroxyalkyl, amino, alkylamino, dialkylamino and hydroxyalkylamino; especially unsubstituted phenyl or phenyl substituted with one, two, or three substituents each independently selected from the group alkyl, alkoxy, alkoxycarbonyl, cyano, halogen, haloalkyl, amino, alkylamino, dialkylamino and hydroxyalkylamino; preferably unsubstituted phenyl or phenyl substituted with one, two or three substituents each independently selected from the group consisting of C$_{1-4}$ alkyl, C$_{1-4}$ alkoxy, cyano, halogen, halo(C$_{1-4}$)alkyl, hydroxy, and hydroxy(C$_{1-4}$)alkyl; and preferably phenyl substituted with one or two substituents each independently selected from the group consisting of methyl, ethyl, isopropyl, tert-butyl, n-butyl, methoxy, ethoxy, cyano, chlorine, fluorine, bromine, chloromethyl, chloroethyl, fluoromethyl, fluoroethyl, difluoromethyl, 1,1-difluoroethyl, 2,2-difluoroethyl, trifluoromethyl, 2,2,2-trifluoroethyl, hydroxy, hydroxymethyl, and 2-hydroxyethyl.

Useful heteroaryl groups for R$^2$ include 5- to 14-membered heteroaryl groups optionally substituted with one, two or three substituents each independently selected from the group consisting of alkyl, alkoxy, alkoxycarbonyl, cyano, halogen, haloalkyl, haloalkoxy, hydroxy, hydroxyalkyl, carboxy, amino, alkylamino, dialkylamino, hydroxyalkylamino, alkylcarbonylamino, alkylcarbonylaminoalkyl, phenyl, phenoxy, heterocyclo and heteroaryl. Suitable heteroaryl groups include, for example, thiazolyl, thiadiazolyl, thiophenyl, isooxazolyl, benzothiazolyl, imidazolyl, benzoxazolyl, pyridyl, pyrimidinyl, quinolinyl, triazolyl, pyrazolyl, benzothiadiazolyl, furyl, benzofuranyl, diazolyl, and benzothiophenyl optionally substituted with one, two or three substituents each independently selected from the group consisting of alkyl, alkoxy, alkoxycarbonyl, cyano, halogen, haloalkyl, haloalkoxy, hydroxy, hydroxyalkyl, carboxy, amino, alkylamino, dialkylamino, hydroxyalkylamino, alkylcarbonylamino, alkylcarbonylaminoalkyl, phenyl, phenoxy, heterocyclo and heteroaryl. Suitable heteroaryl groups include 2-, 3-, or 4-pyridyl optionally substituted with one or two substituents each independently selected from the group consisting of alkyloxycarbonyl, 4-morpholinyl, phenoxy, halogen, alkoxy, alkyl, hydroxy, hydroxyalkyl, cyano, and haloalkyl.

Useful di(C$_{1-6}$)alkylamino groups for R$^2$ include di(C$_{1-4}$)alkylamino groups, such as dimethylamino and diethylamino.

Useful optionally substituted heteroaryl groups for R$^5$ include 1-, 2-, or 3-pyridyl, 2-pyrazinyl, and 3-isoxazolyl.

Exemplary preferred compounds useful in the present invention include:
N-(4-fluorophenyl)-2-[1-(3-trifluoromethyl-benzenesulfonyl)piperidin-4-ylamino]acetamide;
2-{cyclopropyl-[1-(3-trifluoromethyl-benzenesulfonyl)piperidin-4-yl]amino}-N-(4-fluorophenyl)acetamide;
N-(4-fluorophenyl)-2-[1-(3-trifluoromethyl-benzenesulfonyl)-pyrrolidin-3-ylamino]acetamide;
N-(3,5-bis-(trifluoromethyl)phenyl)-2-[1-(3-trifluoromethyl-benzenesulfonyl)piperidin-4-ylamino]acetamide;
N-(2,4-difluorophenyl)-N'-[1-(3-trifluoromethylbenzenesulfonyl)-piperidin-4-yl]malonamide;
and the pharmaceutically acceptable salts, prodrugs and solvates thereof.

Useful cycloalkyl groups are selected from C$_{3-12}$ cycloalkyl. Typical cycloalkyl groups include cyclopropyl, cyclobutyl, cyclopentyl, cyclohexyl, cycloheptyl, and cyclooctyl.

Useful halo or halogen groups include fluorine, chlorine, bromine and iodine.

Useful alkyl groups are selected from straight-chained and branched C$_{1-10}$ alkyl groups, more preferably straight chain C$_{1-6}$ alkyl groups and branched chain C$_{1-6}$ alkyl groups. Typical C$_{1-10}$ alkyl groups include methyl, ethyl, propyl, isopropyl, butyl, sec-butyl, tert-butyl, iso-butyl, 3-pentyl, hexyl and octyl, among others.

Useful alkenyl groups are selected from C$_{2-6}$ alkenyl groups, preferably C$_{2-4}$ alkenyl. Typical C$_{2-4}$ alkenyl groups include ethenyl, propenyl, isopropenyl, butenyl, and sec-butenyl.

Useful alkynyl groups are selected from C$_{2-6}$ alkynyl groups, preferably C$_{2-4}$ alkynyl. Typical C$_{2-4}$ alkynyl groups include ethynyl, propynyl, butynyl, and 2-butynyl groups.

Useful arylalkyl groups include any of the above-mentioned C$_{1-10}$ alkyl groups substituted by any of the C$_{6-14}$ aryl groups mentioned below. Typical arylalkyl groups include benzyl, phenethyl, and naphthylmethyl.

Useful arylalkenyl groups include any of the above-mentioned C$_{2-6}$ alkenyl groups substituted by any of the C$_{6-14}$ aryl groups mentioned below.

Useful arylalkynyl groups include any of the above-mentioned C$_{2-6}$ alkynyl groups substituted by any of the C$_{6-14}$ aryl groups mentioned below.

Useful cycloalkylalkyl groups include any of the above-mentioned C$_{1-10}$ alkyl groups substituted by any of the above-mentioned cycloalkyl groups.

Useful haloalkyl groups include any of the above-mentioned C$_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl and trichloromethyl groups).

Useful hydroxyalkyl groups include any of the above-mentioned C$_{1-10}$ alkyl groups substituted by hydroxy (e.g., hydroxymethyl, hydroxyethyl, hydroxypropyl and hydroxy-butyl groups, and especially hydroxymethyl, 1-hydroxyethyl, 2-hydroxypropyl, 3-hydroxybutyl, and 2-hydroxy-1-methylpropyl).

Useful alkoxy groups include oxygen substituted by one of the $C_{1-10}$ alkyl groups mentioned above.

Useful alkoxyalkyl groups include any of the above-mentioned $C_{1-10}$ alkyl groups substituted with any of the above-mentioned alkoxy groups.

Useful haloalkoxy groups include oxygen substituted by one of the $C_{1-10}$ haloalkyl groups mentioned above (e.g., fluoromethoxy, difluoromethoxy, and trifluoromethoxy).

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

The term "heteroaryl" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Preferred heteroaryl groups include thienyl, furyl, pyrrolyl, imidazolyl, pyrazolyl, pyridyl, pyrimidinyl, thiazolyl, isothiazolyl, and isoxazolyl.

Useful heteroarylalkyl groups include any of the above-mentioned $C_{1-10}$ alkyl groups substituted by any of the heteroaryl groups mentioned below. Useful values include, for example, 2-pyridylmethyl, 3-pyridylmethyl, 4-pyridylmethyl.

The terms "heterocyclic" and "heterocyclo" are used herein to mean saturated or wholly or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. Examples include, but are not limited to, pyrrolidine, piperidine, piperazine, morpholine, imidazoline, pyrazolidine, benzodiazepines, and the like.

Useful heterocycloalkyl groups include any of the above-mentioned $C_{1-10}$ alkyl groups substituted by any of the above-mentioned heterocyclic groups.

As used herein, the term "amino" or "amino group" refers to —$NH_2$.

Useful aminoalkyl groups include any of the above-mentioned $C_{1-10}$ alkyl groups substituted with an amino group.

Useful diaminoalkyl groups include any of the above-mentioned $C_{1-10}$ alkyl groups substituted with two amino groups.

Useful alkylamino and dialkylamino groups are —$NHR^{22}$ and —$NR^{22}R^{23}$, respectively, wherein $R^{22}$ and $R^{23}$ are each independently selected from a $C_{1-10}$ alkyl group.

Useful alkylaminoalkyl and dialkylaminoalkyl groups are any of the above-mentioned $C_{1-10}$ alkyl groups substituted by any of the above-mentioned alkylamino and dialkylamino groups, respectively.

Useful aminocarbonylalkyl groups include any of the above-mentioned $C_{1-10}$ alkyl groups substituted with an aminocarbonyl group, i.e., —$C(O)NH_2$.

Useful alkylcarbonyl groups include a carbonyl group, i.e., —C(O)—, substituted by any of the above-mentioned $C_{1-10}$ alkyl groups.

Useful alkylcarbonylamino groups include any of the above-mentioned alkylcarbonyl groups attached to an amino nitrogen, such as methylcarbonylamino.

Useful mercaptoalkyl groups include any of the above-mentioned $C_{1-10}$ alkyl groups substituted by a —SH group.

As used herein, the term "carboxy" refers to —COOH.

Useful carboxyalkyl groups include any of the above-mentioned $C_{1-10}$ alkyl groups substituted by —COOH.

As used herein, the term "ureido" refers to —NH—C(O)—$NH_2$.

As used herein, the term "azido" refers to —$N_3$.

As used herein, the term "optionally substituted" refers to a group that may be unsubstituted or substituted.

Optional substituents on optionally substituted groups, when not otherwise indicated, include one or more groups, preferably 1, 2, or 3 groups, independently selected from the group consisting of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, amino($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, azido, alkoxy, carboxy, aminocarbonyl, and mercapto($C_{1-6}$)alkyl groups mentioned above. Preferred optional substituents include halo, halo($C_{1-6}$)alkyl, hydroxy ($C_{1-6}$)alkyl, amino($C_{1-6}$)alkyl, hydroxy, nitro, $C_{1-6}$ alkyl, alkoxy, and amino.

The invention disclosed herein is also meant to encompass prodrugs of any of the disclosed compounds. As used herein, prodrugs are considered to be any covalently bonded carriers that release the active parent drug in vivo. Non-limiting examples of prodrugs include esters or amides of compounds of any of Formulae I-VI having hydroxyalkyl or aminoalkyl as a substituent, and these may be prepared by reacting such parent compounds with anhydrides such as succinic anhydride.

The invention disclosed herein is also intended to encompass any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^3H$, $^{11}C$, and $^{14}C$. Isotopically-labeled compounds of the present invention can be prepared by methods known in the art.

The present invention is also directed specifically to $^3H$, $^{11}C$, or $^{14}C$ radiolabeled compounds of any of Formulae I-VI, as well as their pharmaceutically acceptable salts, prodrugs and solvates, and the use of any such compounds as radioligands for their binding site on the calcium channel. For example, one use of the labeled compounds of the present invention is the characterization of specific receptor binding. Another use of a labeled compound of the present invention is an alternative to animal testing for the evaluation of structure-activity relationships. For example, the receptor assay may be performed at a fixed concentration of a labeled compound of the invention and at increasing concentrations of a test compound in a competition assay. For example, a tritiated compound of any of Formulae I-VI can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A),* Chapter 6 (1987). $^{14}$C-labeled compounds can be prepared by employing starting materials having a $^{14}$C carbon.

Some of the compounds disclosed herein may contain one or more asymmetric centers and may thus give rise to enantiomers, diastereomers, and other stereoisomeric forms. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" is meant to encompass administering to a subject a compound of the present invention for the purposes of amelioration or cure, including preemptive and palliative treatment.

The invention disclosed herein also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and he like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. One type of solvate is a hydrate. Solvates typically do not significantly alter the physiological activity or toxicity of the compounds, and as such may function as pharmacological equivalents.

Since compounds of Formulae I-VI are blockers of calcium ($Ca^{2+}$) channels, a number of diseases and conditions mediated by calcium ion influx can be treated by employing these compounds. The present invention is thus directed generally to a method for treating a disorder responsive to the blockade of calcium channels, and particularly the selective blockade of N-type calcium channels, in an animal suffering from, or at risk of suffering from, said disorder, said method comprising administering to the animal an effective amount of a compound represented by any of defined Formulae I-VI, or a pharmaceutically acceptable salt, prodrug or solvate thereof.

The present invention is further directed to a method of modulating calcium channels, especially N-type calcium channels, in an animal in need thereof, said method comprising administering to the animal at least one compound represented by any of defined Formulae I-VI, or a pharmaceutically acceptable salt, prodrug or solvate thereof.

More specifically, the present invention provides a method of treating stroke, the neuronal damage resulting from head trauma, epilepsy, pain (e.g., acute pain, chronic pain, which includes but is not limited to neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In one embodiment, the invention provides a method of treating pain. In another embodiment, the type of pain treated is chronic pain. In another embodiment, the type of pain treated is neuropathic pain. In another embodiment, the type of pain treated is inflammatory pain. In another embodiment, the type of pain treated is surgical pain. In another embodiment, the type of pain treated is acute pain. In another embodiment, the treatment of pain (e.g., chronic pain, such as neuropathic pain or inflammatory pain, acute pain or surgical pain) is preemptive. In another embodiment, the treatment of pain is palliative. In each instance, such method of treatment requires administering to an animal in need of such treatment an amount of a compound of the present invention that is therapeutically effective in achieving said treatment. In one embodiment, the amount of such compound is the amount that is effective as to block calcium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain, In: Textbook of Pain*, Wall and Melzack eds., 3rd ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to the use of a compound represented by any of defined Formulae I-VI, or a pharmaceutically acceptable salt, prodrug or solvate thereof, in the manufacture of a medicament for treating a disorder responsive to the blockade of calcium channels (e.g., any of the disorders listed above) in an animal suffering from said disorder. In one embodiment, the disorder is responsive to the selective blockade of N-type calcium channels.

Furthermore, the present invention is directed to a method of modulating calcium channels, especially N-type calcium channels, in an animal in need thereof, said method comprising administering to the animal at least one compound represented by any defined Formulae I-VI, or a pharmaceutically acceptable salt, prodrug or solvate thereof.

The present invention is also directed to the use of a compound represented by any of defined Formulae I-VI, or a pharmaceutically acceptable salt, prodrug or solvate thereof, in the manufacture of a medicament, in particular a medicament for modulating calcium channels, especially N-type calcium channels, in an animal in need thereof.

Synthesis of Compounds

The compounds of the present invention may be prepared using methods known to those skilled in the art in view of this disclosure. For example, compounds of Formula I where Z is $Z^1$ can be prepared as shown in Schemes 1-4.

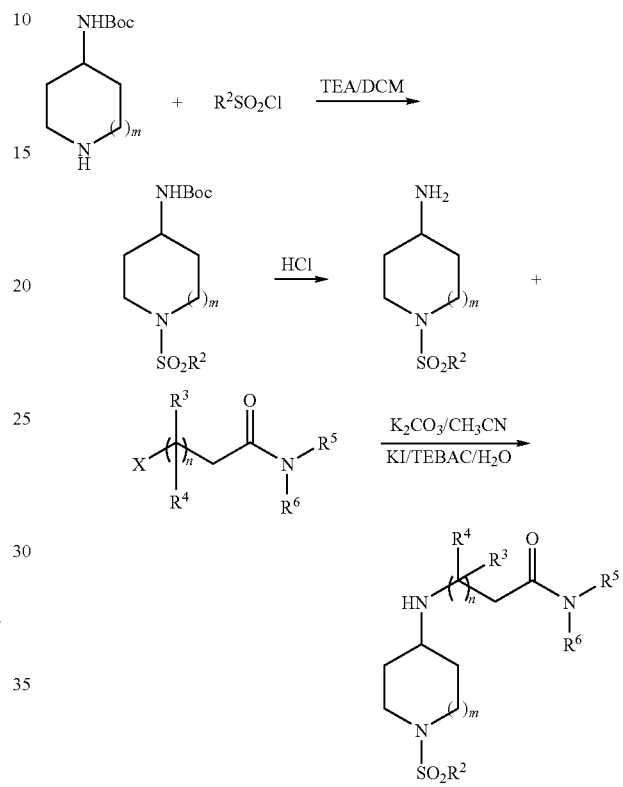

where m, n, and $R^1$-$R^6$ are as defined above for Formula I, and X is halogen, such as chlorine. The protecting group is removed by HCl in an appropriate solvent and the free amine is reacted with an appropriate chloride starting material to give the compounds of Formula I. TEBAC (benzyltriethylammonium chloride) can be purchased from ACROS.

Compounds of Formula I where Z is $Z^1$ can be prepared as follows:

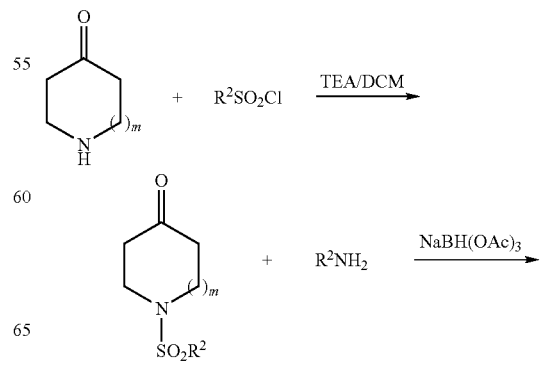

-continued

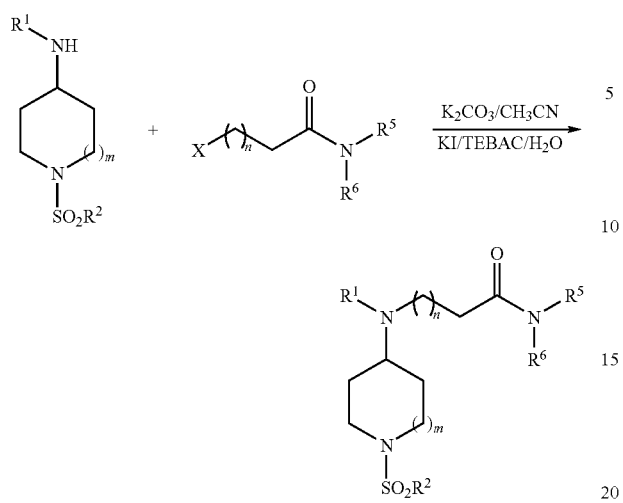

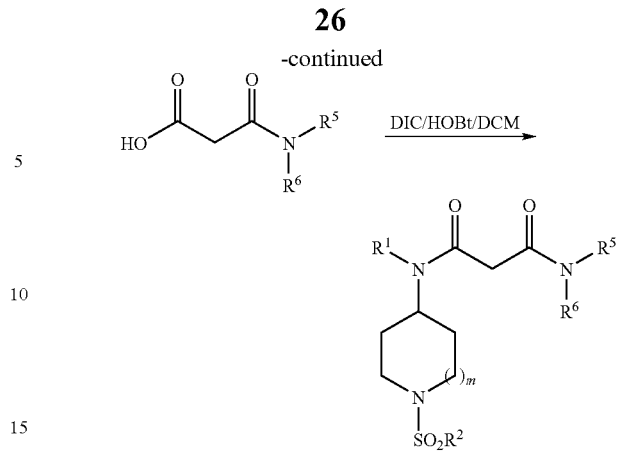

where $R^1$, $R^2$, $R^5$, $R^6$ and n are as defined for Formula I and X is halogen, such as chlorine.

Compounds of Formula I where Z is $Z^1$ can also be prepared as shown in Scheme 3:

where $R^1$, $R^2$, $R^5$, $R^6$ and m are as defined for Formula I. The reaction is conducted in the presence of diisopropyl azodicarboxylate, triethylamine and 1-hydroxybenzotriazole in an appropriate solvent, such as dichloromethane, at room temperature. Suitable starting materials can be prepared, for example, as shown in Examples 1 and 5 below.

A method for preparing compounds of Formula I where Z is $Z^2$ can be as follows:

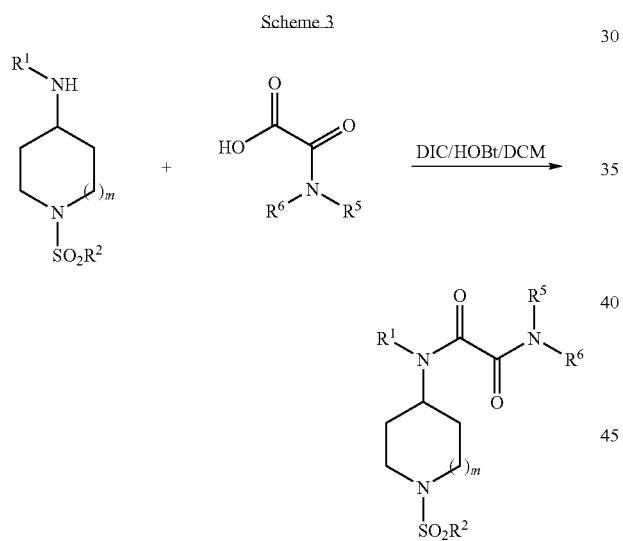

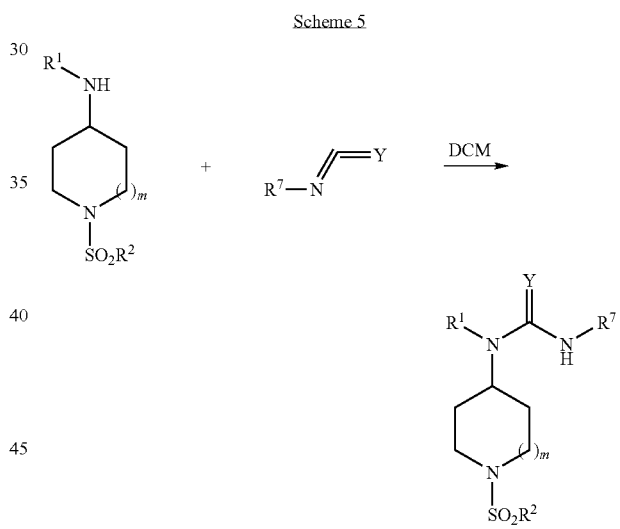

where $R^1$, $R^2$, $R^5$, $R^6$ and m are as defined above.

Further compounds of Formula I where Z is Z can be prepared as follows:

where $R^1$, $R^2$, $R^7$, Y and m are as defined for Formula I.

Compounds of Formula I where Z is $Z^3$ and r is 0 can be prepared as shown in Scheme 6:

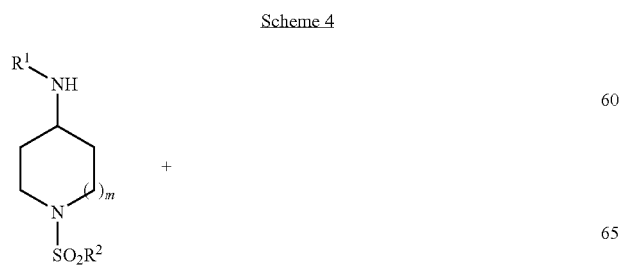

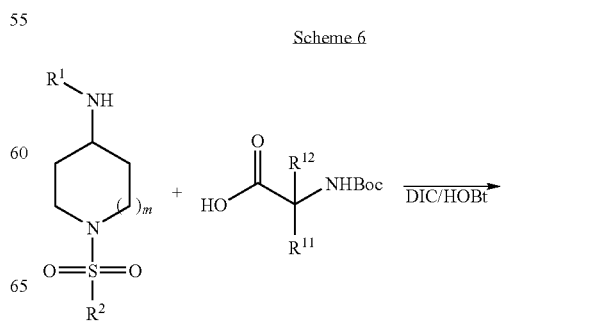

27

-continued

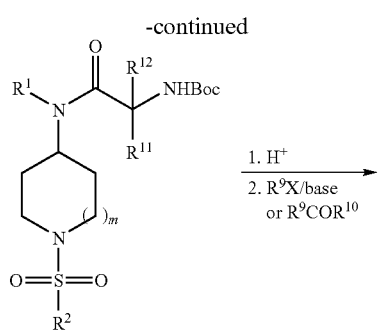

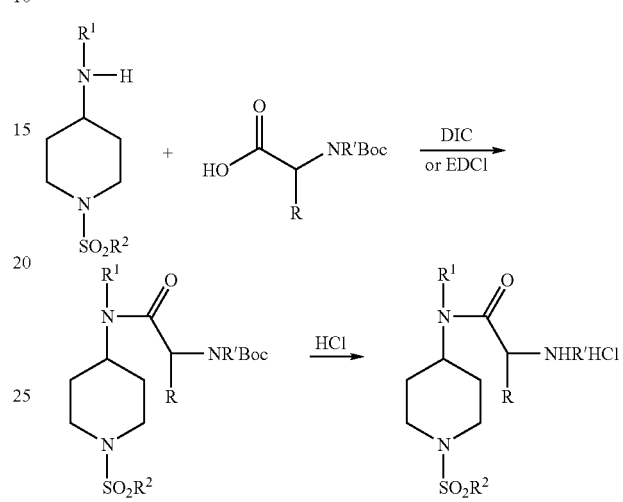

where $R^1$, $R^2$, $R^9$-$R^{12}$, and m are as defined above for Formula I, and X is Cl, Br, I, or —$OSO_2CF_3$.

Compounds of Formula V can be prepared as shown in Scheme 7:

28 where $R^2$, $R^9$ and m are as defined above for Formula V; $w^1$ and $w^2$ are each independently Cl, Br, or OH; $w^3$ and $w^4$ are each independently H, F, or OH, and t is 0 or 1. Compounds of Formula VI can be prepared using a procedure similar to that described above in Scheme 7 and appropriate reagents.

Further, compounds of Formula I where Z is $Z^3$ can be prepared as shown in Scheme 8:

Scheme 8

Scheme 7

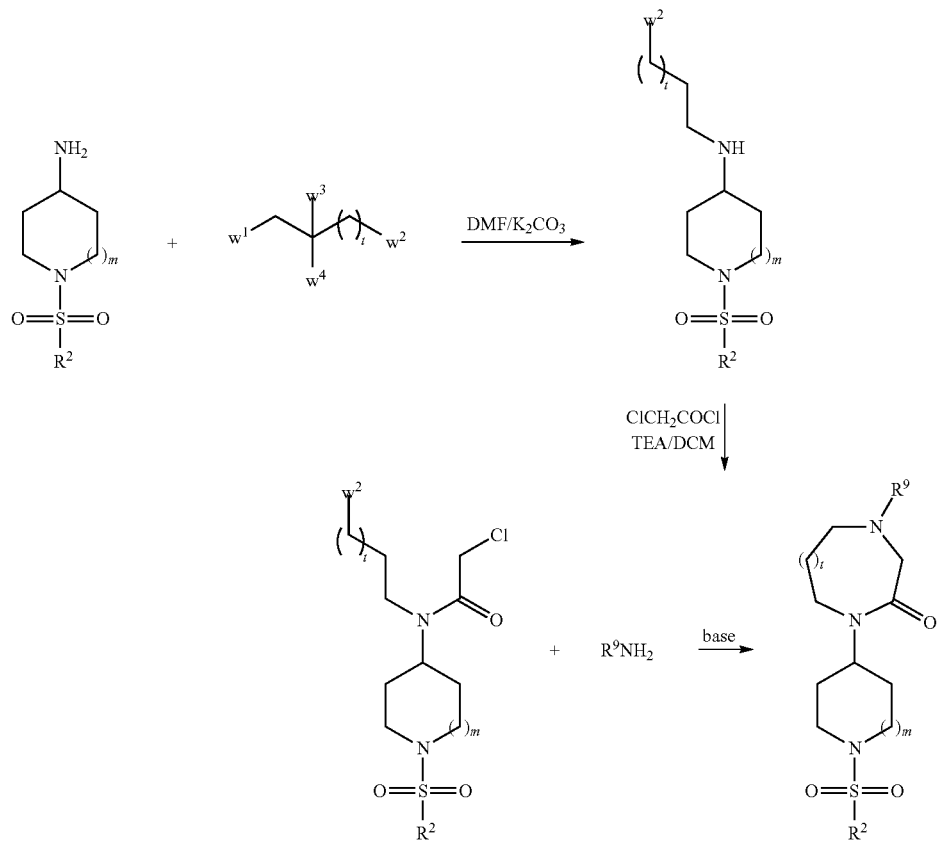

where R¹ and R² are as defined above for Formula I, R is hydrogen, alkyl, hydroxyalkyl, alkoxyalkyl, haloalkyl, aminoalkyl, cycloalkyl, optionally substituted phenyl, optionally substituted benzyl, or benzyloxyalkyl and R' is hydrogen, alkyl, alkenyl, hydroxyalkyl, haloalkyl, aminoalkyl or phenyl.

Further, compounds of Formula I where Z is Z³ can be prepared as shown in Scheme 9:

Scheme 9

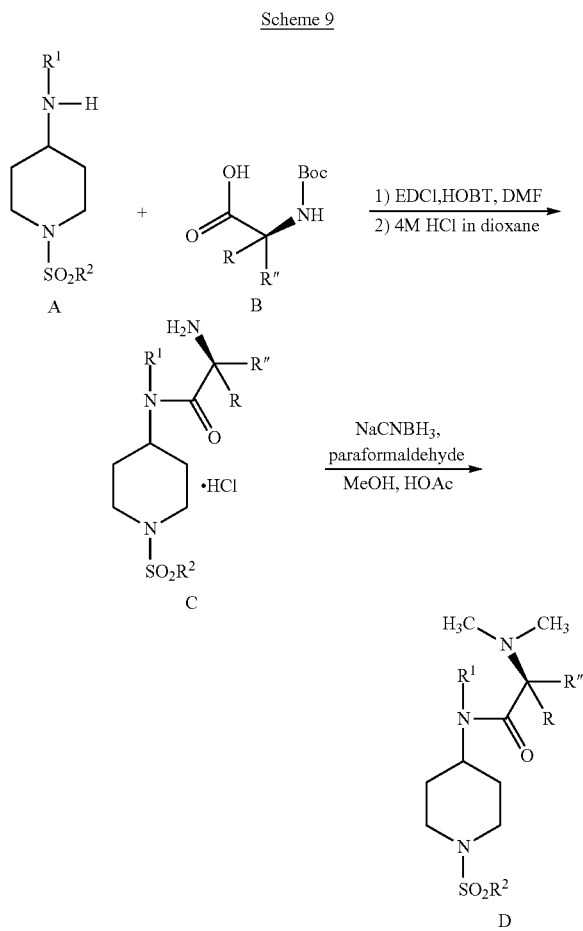

where R¹ and R² are as defined above for Formula I, R is hydrogen, alkyl, hydroxyalkyl, alkoxyalkyl, haloalkyl, aminoalkyl, cycloalkyl, optionally substituted phenyl, optionally substituted benzyl, or benzyloxyalkyl, and R" is hydrogen, or R and R" together with the carbon atom to which they are attached form a $C_{3-7}$ cycloalkyl group.

Further, compounds of Formula I where Z is Z³ can be prepared as shown in Scheme 10:

Scheme 10

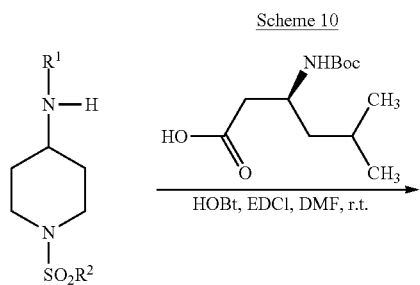

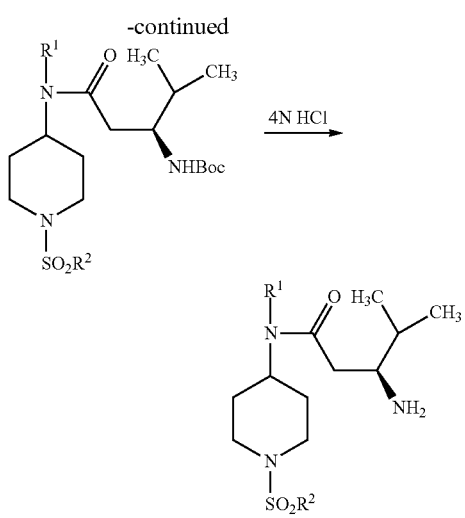

where R¹ and R² are as defined above for Formula I.

The method of Scheme 10 is similar to that described in Scheme 8 except that the starting amino acid is a β-amino acid instead of an α-amino acid.

Testing of Compounds

Compounds of the present invention were assessed by calcium mobilization and/or electrophysiological assays for calcium channel blocker activity. One aspect of the present invention is based on the use of the compounds herein described as N-type calcium channel blockers. In one aspect of the present invention, it has been found that certain compounds herein described show selectivity as N-type calcium channel blockers. Based upon this property, these compounds are considered useful in treating stroke, neuronal damage resulting from head trauma, migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also expected to be effective in treating pain, such as acute pain, chronic pain, which includes but is not limited to neuropathic pain and inflammatory pain, or surgical pain.

More specifically, the present invention is directed to compounds of Formulae I-VI that are blockers of calcium channels. According to the present invention, those compounds having preferred N-type calcium channel blocking properties exhibit an $IC_{50}$ of about 100 μM or less in the calcium mobilization and/or electrophysiological assays described herein. Preferably, the compounds of the present invention exhibit an $IC_{50}$ of 10 μM or less. More preferably, the compounds of the present invention exhibit an $IC_{50}$ of about 6 μM or less. Most preferably, the compounds of the present invention exhibit an $IC_{50}$ of about 1.0 μM or less. Compounds of the present invention can be tested for their N-type and L-type $Ca^{2+}$ channel blocking activity by the following calcium mobilization and/or electrophysiological assays.

In one embodiment, compounds useful in the present invention are those represented by any one of Formulae I-VI that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an $IC_{50}$ for L-type channel blocking activity for a compound of the present invention over an $IC_{50}$ for N-type channel blocking activity for the same compound is more than 1, i.e., LTCC $IC_{50}$/NTCC $IC_{50}$>1. Preferably, compounds of the present invention exhibit an LTCC $IC_{50}$/NTCC $IC_{50}$ ratio of about 2 or more, about 10 or more, about 20 or more, about 30 or more, about 50 or more, or about 100 or more.

Calcium Mobilization and Electrophysiological Assay Protocols:

Cell maintenance and differentiation. Unless noted otherwise, cell culture reagents were purchased from Mediatech of Herndon, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 µg/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 µM bromodeoxyuridine (Sigma). Cells were differentiated for 8 days by replacing differentiation medium every 2-3 days.

A7r5 (ATCC) cells were maintained and routinely cultured in A7r5 growth medium consisting of Dulbecco's Modified Eagles Medium containing 10% FBS, 100 U/mL penicillin, 100 µg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

Recombinant human embryonal kidney cells (HEK293, ATCC) stably transfected with either N-type calcium channel (NTCC) subunits (α1b, α2δ, and β3) or L-type calcium channel (LTCC) subunits (α1c, α2δ, and β1) were routinely cultured in growth medium consisting of Dulbecco's Modified Eagles Medium containing 10% FBS, 100 U/mL penicillin, 100 µg/mL streptomycin, 4 mM L-glutamine, 500 µg/mL geneticin (G418), 20 µg/mL Blasticidin S (InVivogen, San Diego, Calif.) and 500 µg/mL zeocin (InVivogen).

FLIPR Calcium Mobilization Assay for N-type Calcium Channel. One day prior to performing this assay, differentiated IMR32 cells were treated with 1× CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of IMR32 buffer, 0.05 mL of each compound tested diluted in IMR32 buffer containing 20 µM nitrendipine (Sigma), and 0.1 mL KCl dissolved in IMR32 buffer, plus Fluo-4 were added (3 µM final concentration, Molecular Probes, Eugene, Oreg.). Final test compound concentrations ranged from about 846 µM to about 17 µM, final nitrendipine concentration was 5 µM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing IMR32 buffer. Plates were then transferred to a Fluorimetric Imaging Plate Reader (FLIPR[96], Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 pM to about 17 µM, final nitrendipine concentration was 5 µM, and final KCl concentration was 90 mM. Data were collected over the entire time course and analyzed using Excel, Graph Pad Prism (version 3.02, Graph Pad, San Diego, Calif.), or an in-house non-linear regression analysis software.

FLIPR Calcium Mobilization Assay for L-type Calcium Channel. One day prior to performing this assay, HEK293 cells stably expressing recombinant rat L-type calcium channel (LTCC) subunits (α1c, α2δ, and β1) were trypsinized, then seeded on poly-D-lysine-coated 96-well clear-bottom black plates (Becton Dickinson, Franklin Lakes, N.J.) at 75,000 cells/well. On the day of the assay, the plates were washed with LTCC wash buffer (127 mM NaCl, 2 mM $MgCl_2$, 700 µM NaH2PO4, 5 mM $CaCl_2$, 5 mM $NaHCO_3$, 8 mM HEPES, 10 mM glucose, pH 7.4), then loaded with 0.1 mL of LTCC wash buffer containing Fluo-4 (3 µM final concentration, Molecular Probes, Eugene, Oreg.). After 1 hour, the cells were washed with 0.1 mL LTCC wash buffer and resuspended in 0.05 mL LTCC assay buffer (same composition as LTCC wash buffer). Plates were then transferred to a FLIPR[96] for assay. The FLIPR measured basal Fluo-4 fluorescence for 15 seconds, then added 0.05 mL of each compound tested diluted in LTCC assay buffer at final concentrations ranging from about 846 pM to about 17 µM. Fluo-4 fluorescence was then measured for 5 minutes. 0.1 mL KCl agonist dissolved in LTCC assay buffer was then added to the cells to produce a final concentration of 90 mM KCl, and fluorescence was measured for another 45 seconds. Data were collected over the entire time course and analyzed using Excel, Graph Pad Prism, or an in-house regression analysis software.

Alternative FLIPR Calcium Mobilization Assay for L-type Calcium Channel. Alternatively, the following cell line and procedure may be used for the FLIPR calcium mobilization assay for L-type calcium channel. One day prior to performing this assay, differentiated A7r5 cells are trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates are washed with A7r5 wash buffer (127 mM NaCl, 2 mM $MgCl_2$, 700 µM NaH2PO4, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 µM final concentration, Molecular Probes, Eugene, Oreg.). After 1 hour, the cells are washed with 0.1 mL A7r5 wash buffer and resuspended in 0.05 mL A7r5 assay buffer that is composed of A7r5 wash buffer plus 50 µM valinomycin (Sigma). Plates are then transferred to a FLIPR[96] for assay. The FLIPR measures basal Fluo-4 fluorescence for 15 seconds, then adds 0.05 mL of each compound tested diluted in A7r5 assay buffer at final concentrations ranging from about 846 pM to about 17 µM. Fluo-4 fluorescence is then measured for 5 minutes. 0.1 mL KCl agonist dissolved in A7r5 assay buffer is then added to the cells to produce a final concentration of 90 mM KCl, and fluorescence was measured for another 45 seconds. Data were collected over the entire time course and analyzed using Excel, Graph Pad Prism, or an in-house regression analysis software.

Cloning of N- and L-type calcium channel subunit open reading frame cDNAs. Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by Dubel et al. in *Proc. Natl. Acad. Sci. U.S.A* 89: 5058-5062 (1992). The beta1 subunit cDNA has been described by Pragnell et al. in *FEBS Lett.* 291: 253-258 (1991). The beta3 subunit cDNA has been described by Castellano et al. in *J. Biol. Chem.* 268: 12359-12366 (1993). The alpha2delta subunit cDNA has been described by Kim et al. in *Proc. Natl. Acad. Sci. U.S.A.* 89: 3251-3255 (1992). The alpha1c subunit cDNA has been described by Koch et al. in *J. Biol. Chem.* 265: 17786-17791 (1990).

The 7.0 kb cDNA containing the entire α1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "+A ΔSFMG SET" according to the nomenclature of Lin et al. (*Neuron* 18: 153-166 (1997)). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen).

The 1.8 kb cDNA encoding the β1 subunit, the 1.45 cDNA encoding the beta3 subunit, and the 3.3 kb cDNA encoding the alpha2delta subunit were cloned by PCR amplification from rat spinal cord cDNA (β1) or brain cDNA (β3, α2δ). Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the α2δ cDNA amplification. PCR products were subcloned and fully sequenced on both strands. Clones matching the reference sequence (β1: NM_017346; β3: NM_012828; α2δ: M86621) and the gene's GenBank rat genomic DNA sequences were recombined into the mammalian expression vector pcDNA3.2DEST (β1, β3) or pcDNA3.1-Zeo (α2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO:11, TABLE 1) and 12 (SEQ ID NO:12, TABLE 1). The PCR fragment was subcloned and fully sequenced on both strands to confirm its identity. A clone matching consensus reference sequence M59786 and rat genomic DNA sequences was recombined into the mammalian expression vector pcDNA6.2DEST. Sequences around the recombinogenic region were sequenced to confirm accurate recombination into the expression vector.

TABLE 1

| PRIMER SEQUENCE | SEQ ID NO. |
| --- | --- |
| CACC ATG GTC CGC TTC GGG GAC | 1 |
| CCG TTC AGT GGC CTC CTC C | 2 |

TABLE 1-continued

| PRIMER SEQUENCE | SEQ ID NO. |
| --- | --- |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-type Recombinant Cell Line Development. N-type calcium channel expressing HEK-293 cells were created in two stages. Stage 1 was created as follows. The rat α1b, and β3 cDNA expression constructs (2.5 μg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 μg/mL blasticidin and 500 μg/mL geneticin, and incubated for 3 weeks at 37° C., 5% $CO_2$, 95% humidity. Plates containing ≦1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 μM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base (version 5.1, IDBS, Parsippany, N.J.) software. The clone with the greatest signal-to-noise ratio, best stability of response with passage number, and best adhesion to PDL precoated plates (Becton Dickinson) was expanded, characterized and used for stage 2 cell line development.

Stage 2 of N-type cell line development was carried out as follows. The rat α2δ cDNA expression construct (5 μg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 μg/mL blasticidin, 500 μg/mL geneticin, and 250 μg/mL zeocin and incubated for 3 weeks at 37° C., 5% $CO_2$, 95% humidity. Plates containing 1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

L-type Recombinant Cell Line Development. L-type calcium channel expressing HEK-293 cells were created in two stages. Stage 1 was created as follows. The rat α1c, and β1 cDNA expression constructs (2.5 μg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 μg/mL blasticidin and 500 μg/mL geneticin, and incubated for 3 weeks at 37° C., 5% $CO_2$, 95% humidity. Plates containing ≦1 clone per well were cultured until wells positive for single clones were confluent. Individual clones were then arrayed into columns of a destination 96-well plate, and partly split into 6-well plates for culture maintenance. Array plates were washed once with LTCC wash (or assay) buffer and cells loaded for 1 hour with 0.1 mL of LTCC buffer containing Fluo-4 (3 μM final concentration, Molecular Probes). Then they were washed twice with 0.1 mL of LTCC buffer, and replaced with 0.1 mL LTCC buffer. Plates were then transferred to a FLIPR[96] for assay. The FLIPR measured basal Fluo-4 fluorescence for 315 seconds, then added 0.1 mL KCl agonist dissolved in LTCC buffer and measured fluorescence for another 45 seconds. Final KCl concentration was 90 mM. Data were collected over the entire time course and analyzed using Excel, Graph Pad Prism, or Activity Base software. The clone with the greatest signal-to-noise ratio, best stability of response with passage number, and best adhesion to PDL precoated plates (Becton Dickinson) was expanded, characterized and used for stage 2 cell line development.

Stage 2 of L-type cell line development was carried out as follows. The rat α2δ cDNA expression construct (5 μg each) was transfected into the stage 1 L-type clonal cell line by Lipofectamine Plus reagent (Invitrogen), as per manufacturer's instructions. 24 hours later, cells were split in limiting dilution into multiple 96-well plates in selection media containing 20 μg/mL blasticidin, 500 μg/mL geneticin, and 250 μg/mL zeocin and incubated for 3 weeks at 37° C., 5% $CO_2$, 95% humidity. Plates containing ≦1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded and characterized.

N-type Electrophysiology in Recombinant Cells. For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (Hamill et al., *Pfluegers Arch.* 391: 85-100 (1981)) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2$GTP (0.5 mM), and adjusted to pH 7.2 with CsOH. The pipette resistance ranged from 2 to 3 MOhm and was compensated by 75-80% by the built-in electronic circuitry.

Currents were elicited by stepping from a holding potential of −90 mV to 0 mV for 20 ms every 20 sec. At the −90 mV membrane voltage about 50% of channels were in the inactivated state, and thus contact with a blocker would involve interaction with both resting and inactivated channels. Every drug was applied at 3 to 4 concentrations increasing in a cumulative manner. Fractional inhibition levels in steady-state were used to draw the partial inhibition concentration curves to get the $IC_{50}$ (i.e. concentration causing 50% reduction in the size of the response) values at −90 mV.

Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned 0.5 mm apart from the cell.

All curve fittings were carried out using Origin software (version 5.0, Microcal). A Hill equation was fit to the concentration-inhibition curves to determine $IC_{50}$ values.

N-type Electrophysiology in Neuronal Cells. To determine dissociation constants in resting versus inactivated state for N-type calcium channels, neuronal cells that endogenously express N-type calcium channels can be used. For electrophysiological recording, the neuronal cells expressing N-type calcium channels are seeded on 35-mm culture Petri dishes at a density of approximately $10^4$ cells/dish and kept in an incubator for up to three days for subsequent recordings. For recordings, the dishes are positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings are made using conventional patch-clamp techniques (Hamill et al., *Pfluegers Arch.* 391: 85-100 (1981)) at room temperature (22-24° C.). The patch-clamp pipettes are pulled from WPI, thick-walled borosilicate glass (WPI, Sarasota, Fla.). Currents are recorded using an Axopatch 200A amplifier (Axon Instruments, Union City, Calif.) and leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes are back-filled with internal solution containing CsCl (110 mM), $MgCl_2$ (3 mM), EGTA (3 mM), HEPES (40 mM), Mg-ATP (4 mM), $Na_2$GTP (0.5 mM), and adjusted to pH 7.2 with CsOH. The pipette resistance ranges from 2 to 3 MOhm and is compensated by 75-80% by the built-in electronic circuitry.

Currents are elicited by stepping from a holding potential of ±90 mV to 0 mV for 20 ms every 10 sec. At the −90 mV membrane voltage a proportion of channels is in the inactivated state, and thus contact with a blocker would involve interaction with both resting and inactivated channels. This protocol is used as a first tier screen. For dissection of two components of inhibition (resting block with the apparent dissociation constant $K_r$, and inactivated state block with $K_i$), steady-state inactivation curves are collected using a double-pulse protocol. Three-second long depolarizing pre-pulse incrementing in 10 mV steps is followed by a 10 ms test pulse to 0 mV.

Stock solutions of each test compound are prepared using DMSO. Serial dilutions to desired concentrations are done with bath solution; concentration of DMSO in final solutions is 0.1%. Drugs are applied by gravity flow using a plane multi-barrel array shooter positioned ~1 mm apart from the cell.

All curve fittings can be carried out using Origin software (version 5.0, Microcal). A Hill equation is used to fit the concentration-response curves and to determine $IC_{50}$ values. A Boltzman equation is used to fit inactivation curves, returning half-inactivation voltage, $V_{0.5}$, slope p and the amplitude of current at the most negative voltage where eventually all channels are in the resting state. These parameters are used to calculate the apparent dissociation constants: $K_r=((Ab/Ac)/(1-(Ab/Ac))*[b])$ where [b] is the drug concentration, Ac is the maximum test current amplitude in control conditions and Ab is the maximum test current amplitude in the presence of a blocker; $K_i=[b]/((exp(-(dx/p))*(1+([b]/K_r))-1)$ where dx is the difference between half-inactivation voltage $V_{0.5}$ in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (10% Tween-80) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (Kim and Chung, *Pain* 50: 355-363 (1992)). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertebral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia: Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia: Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat, prevent or ameliorate the particular disorder. A useful oral dose of a compound of the present invention administered to a mammal is from about 0.0025 to about 50 mg per kg body weight of the mammal, or an equivalent amount of the pharmaceutically acceptable salt, prodrug, or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily, e.g., as one or more tablets or capsules, each containing from about 0.01 to about 50 mg of the compound, or an equivalent amount of a pharmaceutically acceptable salt, prodrug or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal or transmucosal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

A method of the present invention, such as a method for treating a disorder responsive to the blockade of calcium channels in an animal in need thereof, can further comprise administering a second therapeutic agent to the animal in combination with a compound of the present invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A compound of the present invention (i.e., the first therapeutic agent) and the second therapeutic agent can act additively or, in one embodiment, synergistically. In one embodiment, a compound of the present invention is administered concurrently with a second therapeutic agent; for example, a single composition comprising both an effective amount of a compound of any of Formulae I-VI, and an effective amount of the second therapeutic agent can be administered. Accordingly, the present invention further provides a pharmaceutical composition comprising a combination of a compound of the present invention, the second therapeutic agent, and a pharmaceutically acceptable carrier. Alternatively, a first pharmaceutical composition comprising an effective amount of a compound of any of Formulae I-VI and a second pharmaceutical composition comprising an effective amount of the second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the second therapeutic agent is administered while the compound of the present invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazodone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethylstarch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

N-(4-Fluorophenyl)-2-[1-(3-trifluoromethyl-benzenesulfonyl)-piperidin-4-ylamino]acetamide (6)

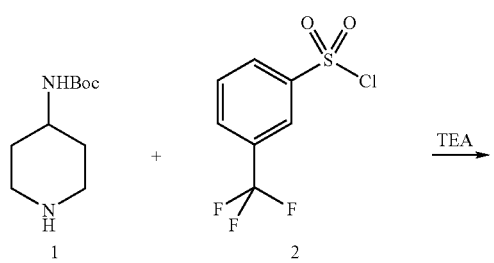

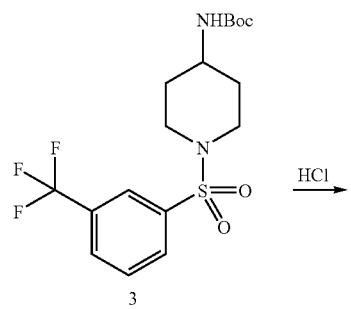

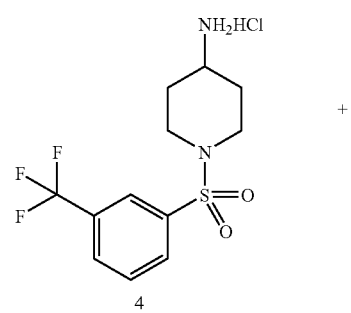

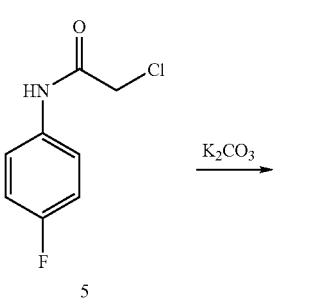

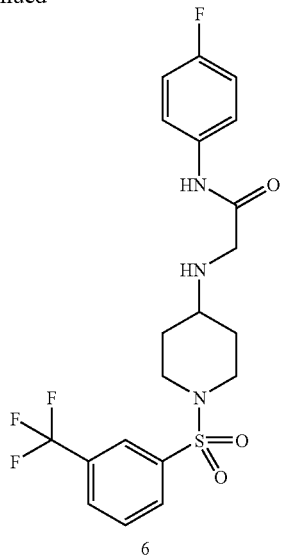

N-(4-Fluoro-phenyl)-2-[1-(3-trifluoromethyl-benzenesulfonyl)-piperidin-4-ylamino]acetamide (6) was prepared as follows. 3-Trifluoromethylphenylsulfonyl chloride (2) (1.7 g, Aldrich) was added to a solution of compound 1 (1.16 g, Aldrich) and triethylamine (TEA, 1 mL) at 0~5° C. The reaction mixture was stirred and warmed to room temperature over 12 hours and then quenched with water (4 mL), extracted with dichloromethane (DCM, 2×10 mL), and washed with brine (6 mL). The organic layer was concentrated to obtain the crude product 3, which was dissolved in 1,4-dioxane (15 mL) and treated with HCl (4N, 4 mL in 1,4-dioxane, Aldrich) at room temperature for 12 hours. The solvents were removed under vacuum, and the residue was washed with Et$_2$O (2×15 mL) to give compound 4 as HCl-salt (white solid).

A mixture of compound 4 (160 mg, 1.0 eq), K$_2$CO$_3$ (400 mg), KI (20 mg) and compound 5 (70 mg, 0.7 eq, Oakwood) in CH$_3$CN (3 mL) was heated and shaken at 40° C. for 48 hours. The reaction mixture was diluted with EtOAc (4 mL), washed with water (2 mL), concentrated under vacuum and purified by column (Silica gel, EtOAc/Hexanes 1/1) to get the title compound 6 as white solid (50 mg, yield 34%). $^1$H NMR (400 MHz, CD$_3$OD): δ 9.09 (br, 1H, NH), 8.02 (s, 1H), 7.95 (d, 1H, 7.9 Hz), 7.87 (d, 1H, 7.7 Hz), 7.70 (dd, 1H, 7.7 & 7.9 Hz), 7.46-7.52 (m, 2H), 7.03 (dd, 2H, 8.5 & 8.9 Hz), 3.76-3.84 (m, 2H), 3.37 (s, 2H), 2.36-2.48 (m, 3H), 1.96-2.04 (m, 2H), 1.48-1.56 (m, 2H); LC: 100%; MS: m/z=460 (M+1).

Example 2

N-(4-Fluorophenyl)-2-[1-(3-trifluoromethylbenzenesulfonyl)-pyrrolidin-3-ylamino]-acetamide (10)

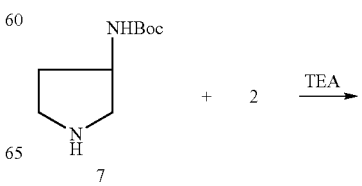

7.9 Hz), 7.51-7.59 (m, 2H), 7.03 (dd, 2H, 8.5 & 8.6 Hz), 3.52-3.58 (m, 1H), 3.36-3.41 (m, 3H), 3.3-3.33 (m, 2H), 3.21-3.26 (m, 1H), 2.01-2.11 (m, 2H), 1.76-1.84 (m, 2H); LC: 100%; MS: m/z=446 (M+1).

Example 3
2-{Cyclopropyl-[1-(3-trifluoromethylbenzenesulfonyl)-piperidin-4-yl]amino}-N-(4-fluorophenyl)acetamide (14)

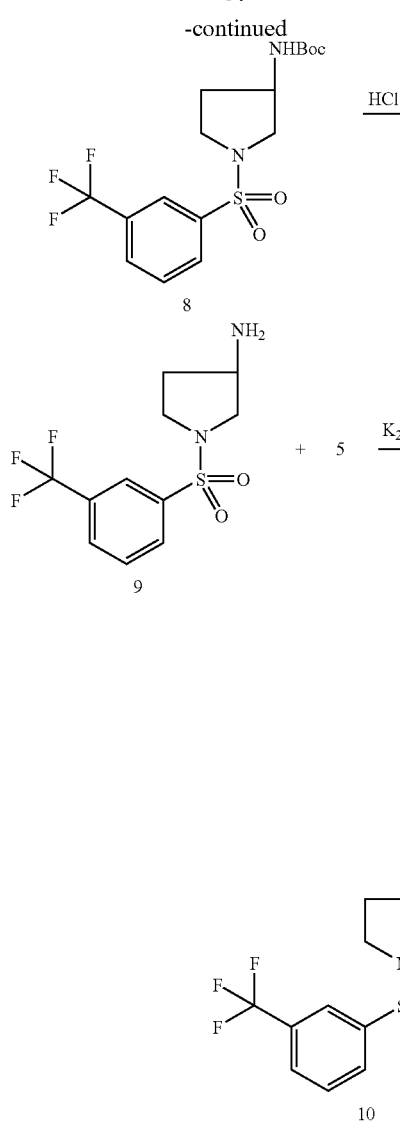
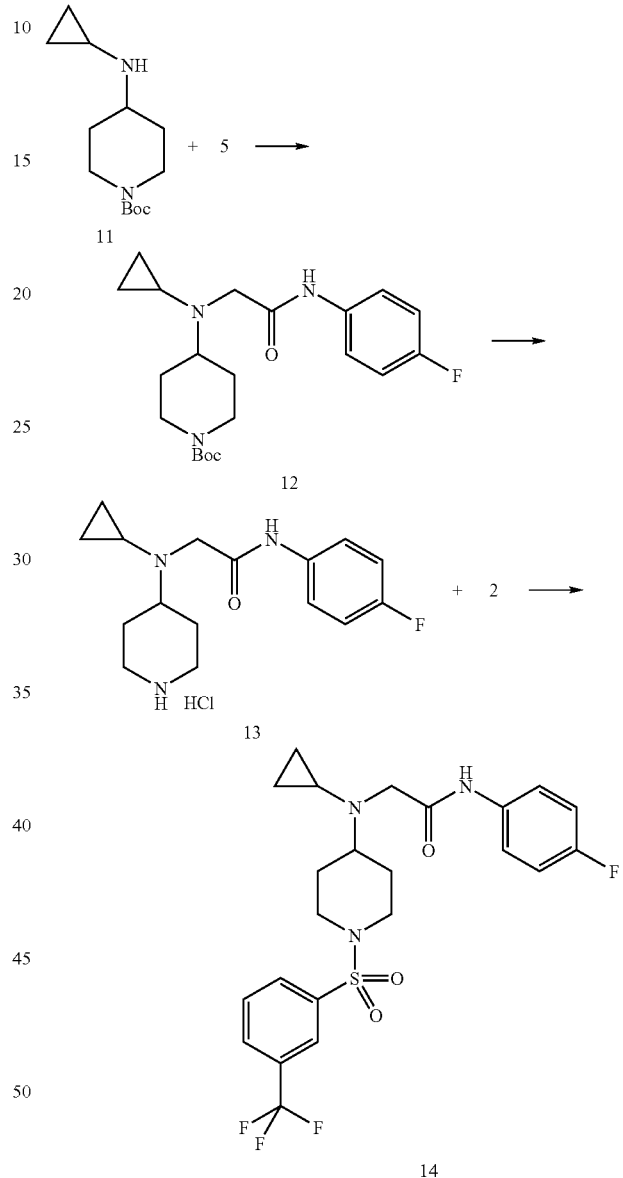

N-(4-Fluorophenyl)-2-[1-(3-trifluoromethylbenzenesulfonyl)-pyrrolidin-3-ylamino]-acetamide (10) was prepared as follows. 3-Trifluoromethylphenylsulfonyl chloride (2) (1.7 g, Aldrich) was added to a solution of compound 7 (1.16 g, Astatech. Inc) and TEA (1 mL) at 0~5° C. The reaction mixture was stirred and warmed to room temperature over 12 hours and then quenched with water (4 mL), extracted with DCM (2×10 mL), and washed with brine (6 mL). The organic layer was concentrated to obtain the crude product 8, which was dissolved in 1,4-dioxane (15 mL) and treated with HCl (4N, 4 mL in 1,4-dioxane, Aldrich) at room temperature for 12 hours. The solvents were removed under vacuum, and the residue was washed with Et₂O (2×15 mL) to give compound 9 as a HCl-salt (white solid).

A mixture of compound 9 (180 mg, 1.0 eq), K₂CO₃ (400 mg), KI (20 mg) and compound 5 (70 mg, 0.7 eq, Oakwood) in CH₃CN (3 mL) was heated and shaked at 40° C. for 48 hours. The reaction mixture was diluted with EtOAc (4 mL), washed with water (2 mL), concentrated under vacuum and purified by column (Silica gel, EtOAc/Hexanes 1/1) to obtain the title compound 10 as white solid (120 mg, yield 72%). $^1$H NMR (400 MHz, CD₃OD): δ 8.93 (br, 1H, NH), 8.12 (s, 1H), 8.03 (d, 1H, 7.9 Hz), 7.86 (d, 1H, 7.7 Hz), 7.70 (dd, 1H, 7.7 &

2-{Cyclopropyl-[1-(3-trifluoromethylbenzenesulfonyl) piperidin-4-yl]amino}-N-(4-fluorophenyl)acetamide (14) was prepared as follows. A mixture of compound 11 (1.1 g, Oakwood), compound 5 (1.0 g), K₂CO₃ (2 g), KI (100 mg) and CH₃CN (15 mL) was heated and stirred at 40° C. for 72 hours. The reaction mixture was diluted with EtOAc (30 mL), washed with water (10 mL), and brine (10 mL). The organic layer was concentrated and purified by column (silica gel, EtOAc/hexanes 1/1) to give compound 12 as a colorless oil. Compound 12 was then dissolved in 10 mL of 1,4-dioxane and treated with 4 mL of HCl (4N in 1,4-dioxane) at room temperature for 12 hours. The solvent was removed under vacuum, the residue was washed with Et₂O (2×20 mL), and the solid was collected and dried to give compound 13 as white solid (HCl-salt).

A mixture of compound 13 (180 mg), TEA (0.5 mL) and compound 2 (0.1 mL) in DCM (2 mL) was shaken at room temperature for 48 hours. The reaction mixture was then washed with water (2 mL) and extracted with EtOAc (2 mL). The combined organic layers were combined and washed with brine (2 mL), concentrated, and purified by column (Silica gel, EtOAc/hexane 1/1) to give the title compound 14 as white solid (100 mg, yield 36%). $^1$H NMR (400 MHz, CD$_3$OD): δ 8.78 (br, 1H, NH), 8.02 (s, 1H), 7.95 (d, 1H, 7.9 Hz), 7.86 (d, 1H, 7.8 Hz), 7.70 (dd, 1H, 7.8 & 7.9 Hz), 7.41-7.44 (m, 2H), 6.99-7.04 (m, 2H), 3.91-3.96 (m, 2H), 3.37 (s, 2H), 2.53-2.60 (m, 1H), 2.26-2.33 (m, 2H), 2.13-2.18 (m, 1H), 1.91-1.96 (m, 2H), 1.76-1.84 (m, 2H), 0.58-0.62 (m, 2H), 0.47-0.51 (m, 2H); LC: 100%; MS: m/z=500 (M+1).

Example 4

N-(3,5-Bis-(trifluoromethyl)phenyl)-2-[1-(3-trifluoromethyl-benzenesulfonyl)piperidin-4-ylamino]acetamide (18)

with water (6 mL), washed with brine (4 mL), concentrated, and purified by column (silica gel, EtOAc/hexanes 1/9) to give compound 17 as colorless oil. A mixture of compound 17 (150 mg), compound 4 (180 mg), K$_2$CO$_3$ (300 mg), and KI (20 mg) in CH$_3$CN (4 mL) was shaken at 40° C. for 72 hours. The reaction mixture was diluted with EtOAc (4 mL), washed with water (2 mL), brine (4 mL), concentrated under vacuum and purified by column (Silica gel, EtOAc/Hexanes 7/3) to obtain the title compound 18 as white solid (100 mg, yield 37%). $^1$H NMR (400 MHz, CD$_3$OD): δ 9.54 (br, 1H, NH), 8.06 (s, 2H), 8.0 (s, 1H), 7.94 (d, 1H, 7.9 Hz), 7.87 (d, 1H, 7.9 Hz), 7.70 (dd, 1H, 7.9 & 7.9 Hz), 7.59 (s, 1H), 3.81-3.84 (m, 2H), 3.42 (s, 2H), 2.45-2.51 (m, 1H), 2.35-2.42 (m, 2H), 1.98-2.04 (m, 2H), 1.49-1.59 (m, 2H); LC: 100%; MS: m/z=578 (M+1).

Example 5

N-(2,4-Difluorophenyl)-N'-[1-(3-trifluoromethylbenzenesulfonyl)-piperidin-4-yl]malonamide (23)

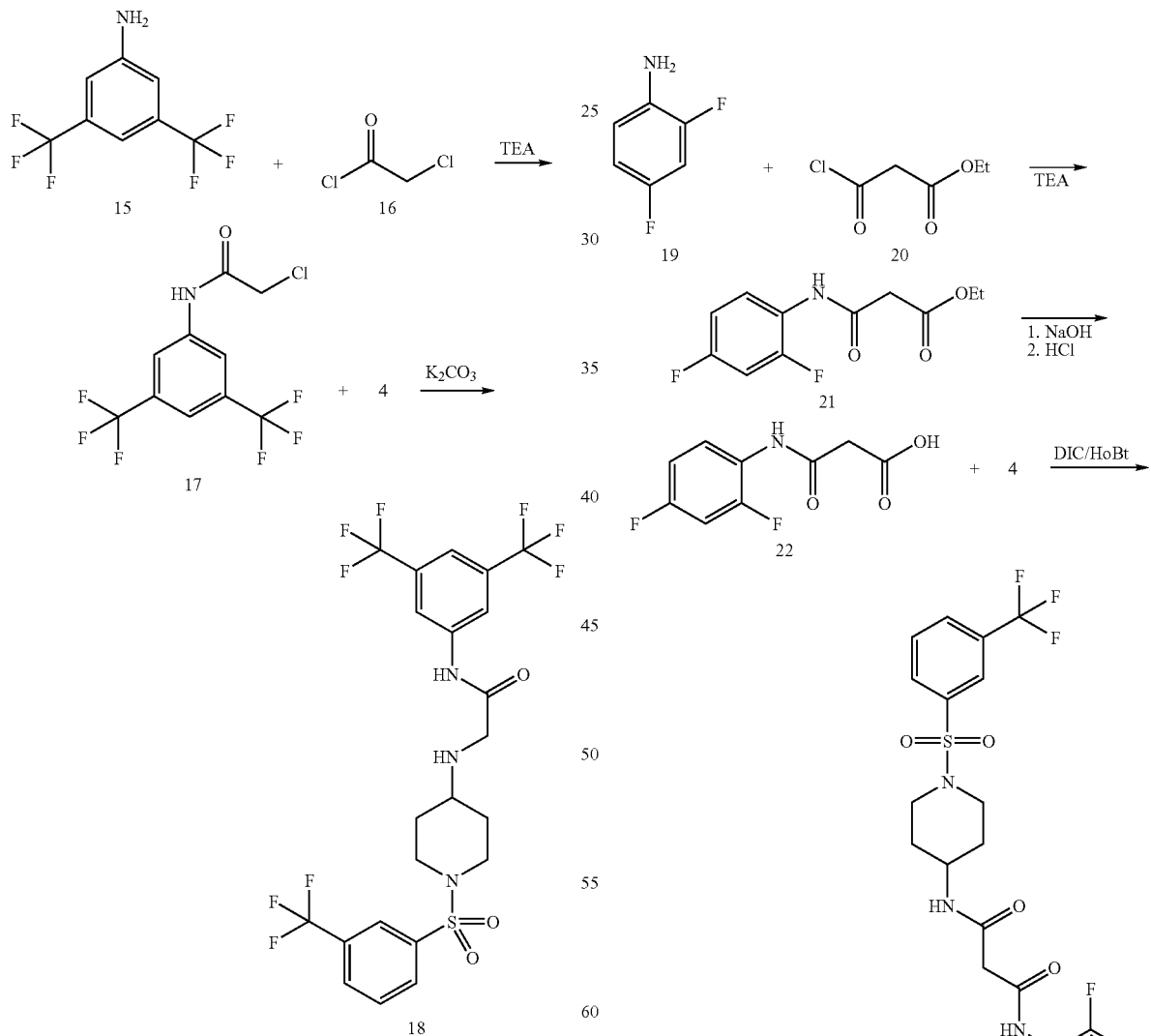

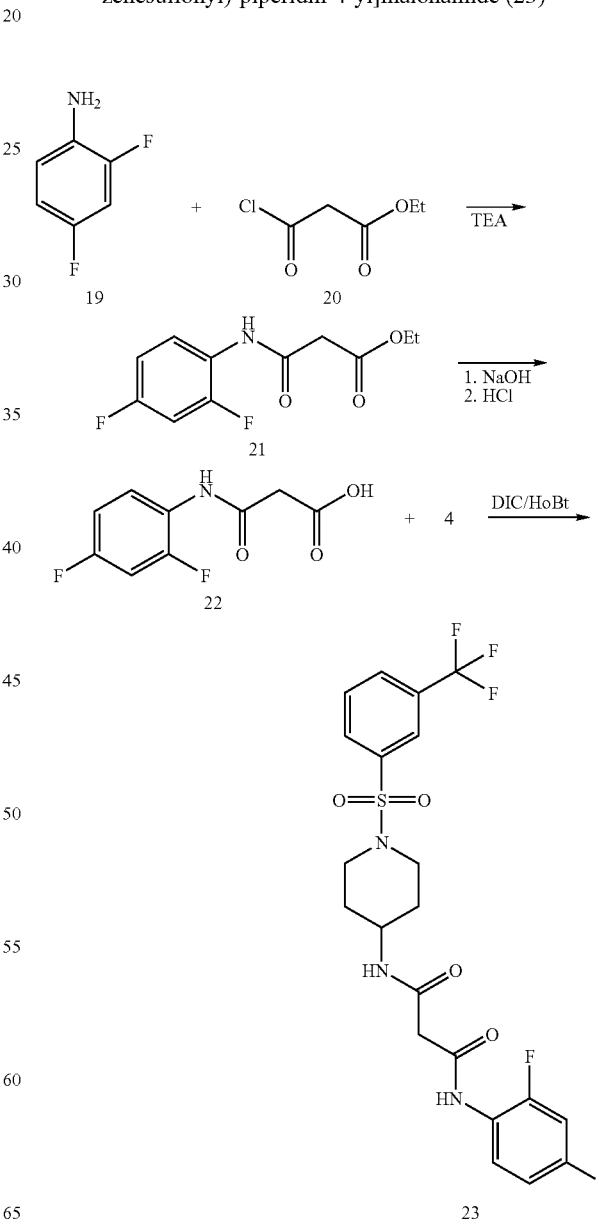

N-(3,5-Bis-(trifluoromethyl)phenyl)-2-[1-(3-trifluoromethyl-benzenesulfonyl)piperidin-4-ylamino]acetamide (18) was prepared as follows. Compound 16 (1.2 g, Aldrich) was added to a solution of compound 15 (2.0 g, Aldrich) and TEA (2 mL) in DCM (20 mL) at 0° C. The reaction mixture was warmed to room temperature over 3 hours and then quenched N-(2,4-Difluorophenyl)-N'-[1-(3-trifluoromethylbenzenesulfonyl)-piperidin-4-yl]malonamide (23) was prepared as follows. Compound 20 (6.0 mL, Aldrich) was added to a solution of compound 19 (5.0 g, Aldrich) and TEA (6 mL) in DCM (30 mL) at 0° C. The reaction mixture was warmed to room temperature over 48 hours and then quenched with water (10 mL), washed with brine (4 mL), concentrated, and purified by column (silica gel, EtOAc/hexanes 3/7) to give compound 21 as white solid (5.0 g).

A solution of compound 21 (5 g, in 25 mL of MeOH) was treated with KOH (2.2 g in 8 mL of water) at room temperature for 24 hours. The solvents were removed under vacuum, water (10 mL) and EtOAc (30 mL) were added to dissolve the residue, and neutralized with HCl (5N aquous) to pH~5. The organic layer was separated, washed with brine, and concentrated to give compound 22 as pale-yellow solid (4.5 g). Diisopropyl azodicarboxylate (DIC, 70 mg) was added to a mixture of compound 22 (100 mg), compound 4 (200 mg), TEA (0.3 mL), 1-hydroxybenzotriazole (HOBt, 30 mg) in DCM (2 mL) at room temperature. The resulting mixture was shaken at room temperature for 48 hours and then the solid was filtered of, the filtrate was concentrated and purified by column (silica gel, EtOAc/hexane 1/1) to give the title compound 23 as white solid (150 mg, yield 65%). $^1$H NMR (400 MHz, CD$_3$OD): δ 9.33 (br, 1H, NH), 8.11-8.17 (m, 1H), 8.02 (s, 1H), 7.95 (d, 1H, 7.9 Hz), 7.89 (d, 1H, 7.9 Hz), 7.72 (dd, 1H, 7.9 & 7.9 Hz), 6.85-6.89 (m, 2H), 6.51 (d, 1H, 7.9 Hz), 3.78-3.84 (m, 3H), 3.32 (s, 2H), 2.45-2.52 (m, 1H), 2.01-2.06 (m, 2H), 1.58-1.65 (m, 2H); MS: m/z=506 (M+1).

Example 6

Compounds of the invention have been tested in the calcium mobilization and/or electrophysiological assay for N-type calcium channel blocking activity, which are described in detail above. Some compounds described have also been tested in the calcium mobilization assay for L-type calcium channel blocking activity, which is described in detail above. Representative values are presented in TABLE 2.

TABLE 2

Evaluation of the tested compounds as N-type calcium channel (NTCC) blockers and L-type calcium channel (LTCC) blockers after a calcium mobilization in vitro assay

| COMPOUND | NTCC IC$_{50}$ (μM) | LTCC IC$_{50}$ (μM) |
|---|---|---|
| N-(4-fluorophenyl)-2-[1-(3-trifluoromethyl-benzenesulfonyl)piperidin-4-ylamino]acetamide (6) | 0.46 | >20 |
| 2-{cyclopropyl-[1-3-trifluoromethyl-benzenesulfonyl)piperidin-4-yl]amino}-N-(4-fluorophenyl)acetamide (14) | 0.79 | 9.33 |
| N-(4-fluorophenyl)-2-[1-(3-trifluoromethyl-benzenesulfonyl)pyrrolidin-3-ylamino]acetamide (10) | 0.47 | 5.98 |
| N-(3,5-bis-(trifluoromethyl)phenyl)-2-[1-(3-trifluoromethylbenzenesulfonyl)piperidin-4-ylamino]acetamide (18) | 0.74 | >20 |
| N-(2,4-difluorophenyl)-N'-[1-(3-trifluoromethyl-benzenesulfonyl)-piperidin-4-yl]malonamide (23) | 1.29 | ND |

ND = not determined

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

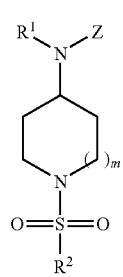

or a pharmaceutically acceptable salt thereof, wherein:

$R^1$ is selected from the group consisting of hydrogen, $C_1$-$C_6$ alkyl, $C_2$-$C_6$ alkenyl, halo($C_1$-$C_6$)alkyl, $C_1$-$C_6$ alkoxy($C_1$-$C_6$)alkyl, halo($C_1$-$C_6$)alkoxy($C_1$-$C_6$)alkyl, hydroxy($C_1$-$C_6$)alkyl, amino($C_1$-$C_6$)alkyl, $C_1$-$C_6$ alkylamino($C_1$-$C_6$)alkyl, di($C_1$-$C_6$)alkylamino($C_1$-$C_6$)alkyl, cycloalkyl, cycloalkenyl, and heterocyclo($C_1$-$C_6$)alkyl, all of which can be optionally substituted;

$R^2$ is selected from the group consisting of $C_1$-$C_6$ alkyl, cycloalkyl, cycloalkenyl, optionally substituted aryl, optionally substituted heteroaryl, and di($C_1$-$C_6$)alkylamino;

Z is selected from the group consisting of $Z^1$, $Z^2$, and $Z^3$ wherein:

$Z^1$ is

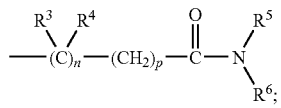

$Z^2$ is

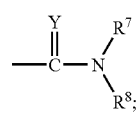

and $Z^3$ is

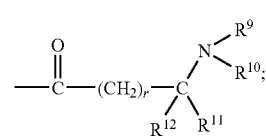

m is 0, 1, or 2;
n is 0, 1 or 2;
p is 0 or 1;
r is 0 or 1;
provided that n and p are not both 0;
$R^3$ and $R^4$ are each independently hydrogen, alkyl, or alkenyl; or
$R^3$ and $R^4$ together form =O; or
$R^3$ and $R^4$ together with the carbon atom to which they are attached form a saturated $C_{3-7}$ cycloalkyl ring optionally substituted with one substituent selected from the group consisting of alkyl, hydroxy, hydroxyalkyl, amino, and =O, wherein one or more carbon atoms of the $C_{3-7}$ cycloalkyl ring are optionally replaced with $NR^{16}$, O, S, or $SO_2$, wherein $R^{16}$ is hydrogen or $C_{1-3}$ alkyl, to form a heterocyclic ring;
$R^5$ is selected from the group consisting of optionally substituted aryl, optionally substituted arylalkyl, and optionally substituted heteroaryl;
$R^6$ is selected from the group consisting of hydrogen, alkyl, alkenyl, optionally substituted cycloalkyl, optionally substituted cycloalkenyl, optionally substituted aryl, optionally substituted arylalkyl, and optionally substituted heteroaryl; or
$R^5$ and $R^6$ together with the nitrogen atom to which they are attached form a heterocyclic ring to give $Z^{11}$ having the structure:

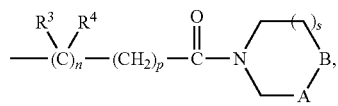

where
A is $CH_2$, CHF, $CF_2$ or CHOH;
B is $CH_2$, O, or N—$R^{51}$, where $R^{51}$ is $CH_3$ or $C(O)CH_3$;
s is 0, 1, or 2;
p is 0 or 1;
$R^3$ is as defined above and $R^4$ is hydrogen;
$R^7$ is selected from the group consisting of alkyl, optionally substituted heterocyclo, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl;
$R^8$ is selected from the group consisting of hydrogen, alkyl, alkenyl, optionally substituted cycloalkyl, optionally substituted cycloalkenyl, optionally substituted aryl, optionally substituted arylalkyl, optionally substituted heteroaryl, and optionally substituted heteroarylalkyl;
(i) $R^9$ and $R^{10}$ are each independently selected from the group consisting of
hydrogen;
hydroxyalkyl;
alkoxyalkyl;
cycloalkyl;
cycloalkenyl, and
phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; or
$R^9$ is hydrogen, alkyl, alkenyl, hydroxyalkyl, alkoxyalkyl, cycloalkyl, cycloalkenyl, or phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; and
$R^{10}$ is $R^{17}$—C(O)—, where
$R^{17}$ is selected from the group consisting of optionally substituted benzyl and optionally substituted benzyloxy; or
$R^9$ and $R^{10}$ together with the nitrogen atom to which they are attached form a 5- or 6-membered heterocyclic ring wherein one or more carbon atoms of the heterocyclic ring are optionally replaced with $NR^{18}$, O, or S, wherein $R^{18}$ is hydrogen or $C_{1-3}$ alkyl;
$R^{11}$ and $R^{12}$ are each independently selected from the group consisting of
hydrogen;
alkyl;
alkenyl;
hydroxyalkyl;
aminoalkyl;
cycloalkyl;
cycloalkenyl;
heterocyclo;
heterocycloalkyl;
phenyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyloxyalkyl;
heteroaryl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; and
heteroarylalkyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; or
$R^{11}$ and $R^{12}$ together form =O; or
$R^{11}$ and $R^{12}$ together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or wherein two adjacent carbon atoms of the $C_{3-7}$ cycloalkyl ring can form a bridge —O— to form a bicyclic ring; or wherein two adjacent carbon atoms of the $C_{3-7}$ cycloalkyl ring together form a fused phenyl group optionally substituted with alkyl, haloalkyl, amino, cyano, or hydroxy; or
$R^{12}$ is hydrogen, alkyl, or alkenyl; $R^9$ is as defined above; and $R^{10}$ and $R^{11}$ together form a bridge —$CH_2$—$CH_2$—$CH_2$— or —$CH_2$—$CHG^1$-$CHG^2$-$CH_2$—, wherein $G^1$ and $G^2$ are both hydrogen or together with the carbon atoms to which they are attached form a fused phenyl group; or (ii) $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ is selected from the group consisting of hydrogen, alkyl, alkenyl, optionally substituted cycloalkyl, optionally substituted cycloalkenyl, optionally substituted aryl, optionally substituted arylalkyl, optionally substituted heteroaryl, and optionally substituted heteroarylalkyl; or $R^9$ and $R^{10}$ together with the nitrogen atom to which they are attached form a heterocyclic ring to give $Z^{31}$ having the structure:

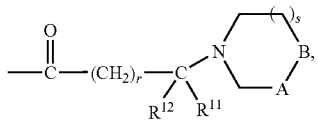

where
A is $CH_2$, CHF, $CF_2$ or CHOH;
B is $CH_2$, O, or N—$R^{51}$, where $R^{51}$ is $CH_3$ or $C(O)CH_3$; and
s is 0, 1, or 2;
r is 0 or 1; and
$R^{11}$ and $R^{12}$ together form =O; or
$R^{11}$ and $R^{12}$ are each independently selected from the group consisting of hydrogen, alkyl, and alkenyl or together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or (iii) $R^{11}$ and $R^{12}$ are both hydrogen or together form =O, $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ and $R^1$ together form a bridge -D-E-G-, wherein D is $CH_2$, C(O), $CHCH_3$, $C(CH_3)_2$ or absent;
E is $CH_2$, C(O), C(S), CHF, $CF_2$ or CHOH; and
G is $CH_2$, C(O), $CHCH_3$, $C(CH_3)_2$ or absent; and
Y is O or S;
with the following provisos:
1) $R^7$ is not optionally substituted 2-thiazolyl or optionally substituted benzothiazolyl;
2) when Z is $Z^2$, $R^2$ is not $C_{1-6}$ alkyl, cycloalkyl or unsubstituted phenyl;
3) when Z is $Z^2$, $R^8$ is hydrogen or alkyl, and $R^7$ is an optionally substituted phenyl or biphenyl, then $R^1$ is other than hydrogen or unsubstituted $C_{1-6}$ alkyl;
4) when Z is $Z^3$ and m is 2, then $R^2$ is not phenyl substituted with CN or $R^9$ and $R^{10}$ are not both hydrogen;
5) when Z is $Z^3$ and $R^9$ and $R^{10}$ are both hydrogen, then $R^1$ is other than hydrogen; or
6) when Z is Z, r is 0, and $R^{11}$ and $R^{12}$ are both hydrogen, then $R^1$ is other than unsubstituted $C_{1-6}$ alkyl.

2. The compound of claim 1 or a pharmaceutically acceptable salt thereof, wherein:

$R^1$ is selected from the group consisting of hydrogen, $C_1$-$C_6$ alkyl, $C_2$-$C_6$ alkenyl, halo($C_1$-$C_6$)alkyl, $C_1$-$C_6$ alkoxy($C_1$-$C_6$)alkyl, halo($C_1$-$C_6$)alkoxy($C_1$-$C_6$)alkyl, hydroxy($C_1$-$C_6$)alkyl, amino($C_1$-$C_6$)alkyl, $C_1$-$C_6$ alkylamino($C_1$-$C_6$)alkyl, di($C_1$-$C_6$)alkylamino($C_1$-$C_6$)alkyl, cycloalkyl, and heterocyclo($C_1$-$C_6$)alkyl, all of which can be optionally substituted;

$R^2$ is selected from the group consisting of $C_1$-$C_6$ alkyl, cycloalkyl, optionally substituted aryl, optionally substituted heteroaryl, and di($C_1$-$C_6$)alkylamino;

Z is selected from the group consisting of $Z^1$, $Z^2$, and $Z^3$ wherein:

$Z^1$ is

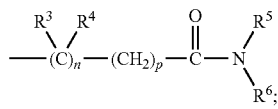

$Z^2$ is

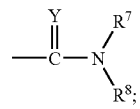

and
$Z^3$ is

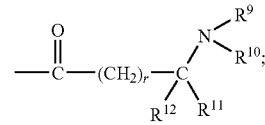

m is 0, 1, or 2;
n is 0, 1 or 2;
p is 0 or 1;
r is 0 or 1;
provided that n and p are not both 0;
$R^3$ and $R^4$ are each independently hydrogen, alkyl, or alkenyl; or
$R^3$ and $R^4$ together form =O; or
$R^3$ and $R^4$ together with the carbon atom to which they are attached form a saturated $C_{3-7}$ cycloalkyl ring optionally substituted with one substituent selected from the group consisting of alkyl, hydroxy, hydroxyalkyl, amino, and =O, wherein one or more carbon atoms of the $C_{3-7}$ cycloalkyl ring are optionally replaced with $NR^{16}$, O, S, or $SO_2$, wherein $R^{16}$ is hydrogen or $C_{1-3}$ alkyl, to form a heterocyclic ring;

$R^5$ is selected from the group consisting of optionally substituted aryl, optionally substituted arylalkyl, and optionally substituted heteroaryl;

$R^6$ is selected from the group consisting of hydrogen, alkyl, alkenyl, optionally substituted cycloalkyl, optionally substituted aryl, optionally substituted arylalkyl, and optionally substituted heteroaryl; or $R^5$ and $R^6$ together with the nitrogen atom to which they are attached form a heterocyclic ring to give $Z^{11}$ having the structure:

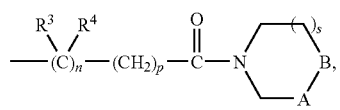

where
A is $CH_2$, CHF, $CF_2$ or CHOH;
B is CH, O, or N—$R^{51}$, where $R^{51}$ is $CH_3$ or $C(O)CH_3$;
s is 0, 1, or 2;
p is 0 or 1;
$R^3$ is as defined above and $R^4$ is hydrogen;
$R^7$ is selected from the group consisting of alkyl, optionally substituted heterocyclo, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl;
$R^8$ is selected, from the group consisting of hydrogen, alkyl, alkenyl, optionally substituted cycloalkyl, optionally substituted aryl, optionally substituted arylalkyl, optionally substituted heteroaryl, and optionally substituted heteroarylalkyl;
(i) $R^9$ and $R^{10}$ are each independently selected from the group consisting of
hydrogen;
hydroxyalkyl;
alkoxyalkyl;
cycloalkyl, and
phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; or
$R^9$ is hydrogen, alkyl, alkenyl, hydroxyalkyl, alkoxyalkyl, cycloalkyl, or phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; and
$R^{10}$ is $R^{17}$—C(O)—, where
$R^{17}$ is selected from the group consisting of optionally substituted benzyl and optionally substituted benzyloxy; or
$R^9$ and $R^{10}$ together with the nitrogen atom to which they are attached form a 5- or 6-membered heterocyclic ring wherein one or more carbon atoms of the heterocyclic ring are optionally replaced with $NR^{18}$, O, or S, wherein $R^{18}$ is hydrogen or $C_{1-3}$ alkyl;
$R^{11}$ and $R^{12}$ are each independently selected from the group consisting of
hydrogen;
alkyl;
alkenyl;
hydroxyalkyl;
aminoalkyl;
cycloalkyl;
heterocyclo;
heterocycloalkyl;
phenyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;
benzyloxyalkyl;
heteroaryl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; and
heteroarylalkyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; or
$R^{11}$ and $R^{12}$ together form =O; or
$R^{11}$ and $R^{12}$ together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or wherein two adjacent carbon atoms of the $C_{3-7}$ cycloalkyl ring can form a bridge —O— to form a bicyclic ring; or wherein two adjacent carbon atoms of the $C_{3-7}$ cycloalkyl ring together form a fused phenyl group optionally substituted with alkyl, haloalkyl, amino, cyano, or hydroxy; or
$R^{12}$ is hydrogen, alkyl, or alkenyl; $R^9$ is as defined above; and $R^{10}$ and $R^{11}$ together form a bridge —$CH_2$—$CH_2$—$CH_2$— or —$CH_2$—$CHG^1$-$CHG^2$-$CH_2$—, wherein $G^1$ and $G^2$ are both hydrogen or together with the carbon atoms to which they are attached form a fused phenyl group; or
(ii) $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and
$R^{10}$ is selected from the group consisting of hydrogen, alkyl, alkenyl, optionally substituted cycloalkyl, optionally substituted aryl, optionally substituted arylalkyl, optionally substituted heteroaryl, and optionally substituted heteroarylalkyl; or
$R^9$ and $R^{10}$ together with the nitrogen atom to which they are attached form a heterocyclic ring to give $Z^{31}$ having the structure:

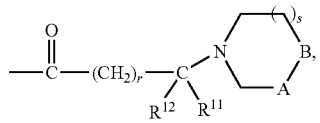

where
A is $CH_2$, CHF, $CF_2$ or CHOH;
B is $CH_2$, O, or N—$R^{51}$, where $R^{51}$ is $CH_3$ or $C(O)CH_3$; and
s is 0, 1, or 2;
r is 0 or 1; and
$R^{11}$ and $R^{12}$ together form =O; or
$R^{11}$ and $R^{12}$ are each independently selected from the group consisting of hydrogen, alkyl, and alkenyl or together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or (iii) $R^{11}$ and $R^{12}$ are both hydrogen or together form =O, $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ and $R^1$ together form a bridge -D-E-G-, wherein D is $CH_2$, C(O), $CHCH_3$, $C(CH_3)_2$ or absent;
E is $CH_2$, C(O), C(S), CHF, $CF_2$ or CHOH; and
G is $CH_2$, C(O), $CHCH_3$, $C(CH_3)_2$ or absent; and
Y is O or S;

with the following provisos:
1) $R^7$ is not optionally substituted 2-thiazolyl or optionally substituted benzothiazolyl;
2) when Z is $Z^2$, $R^2$ is not $C_{1-6}$ alkyl, cycloalkyl or unsubstituted phenyl;
3) when Z is $Z^2$, $R^8$ is hydrogen or alkyl, and $R^7$ is an optionally substituted phenyl or biphenyl, then $R^1$ is other than hydrogen or unsubstituted $C_{1-6}$ alkyl;
4) when Z is $Z^3$ and m is 2, then $R^2$ is not phenyl substituted with CN or $R^9$ and $R^{10}$ are not both hydrogen;
5) when Z is $Z^3$ and $R^9$ and $R^{10}$ are both hydrogen, then $R^1$ is other than hydrogen; or
6) when Z is $Z^3$, r is 0, and $R^{11}$ and $R^{12}$ are both hydrogen, then $R^1$ is other than unsubstituted $C_{1-6}$ alkyl.

3. The compound of claim 1, having the Formula II:

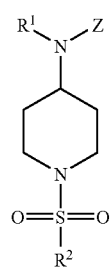

II or a pharmaceutically acceptable salt thereof.

4. The compound of claim 1, having the Formula III:

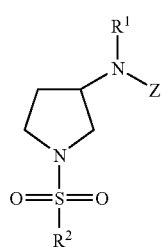

III or a pharmaceutically acceptable salt thereof.

5. The compound of claim 1, having the Formula IV:

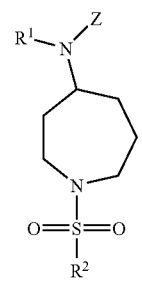

IV or a pharmaceutically acceptable salt thereof.

6. The compound of claim 1, wherein Z is $Z^1$.

7. The compound of claim 6, wherein $Z^1$ is $Z^{11}$ having the structure:

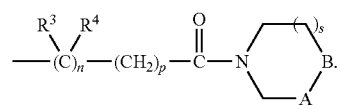

8. The compound of claim 6, wherein $Z^1$ is $Z^{12}$ having the structure:

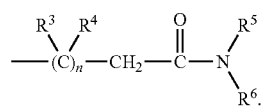

9. The compound of claim 6, wherein $Z^1$ is $Z^{13}$ having the structure:

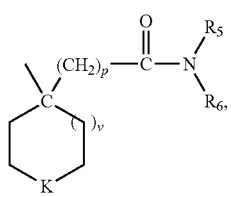

where K is selected from the group consisting of $CH_2$, O, S, $SO_2$, and $NR^{16}$, $R^{16}$ is hydrogen or $C_{1-3}$ alkyl, and v is 0, 1, or 2.

10. The compound of claim 6, wherein $Z^1$ is selected from the group consisting of $Z^{14}$, $Z^{15}$ and $Z^{16}$, wherein:

$Z^{14}$ is

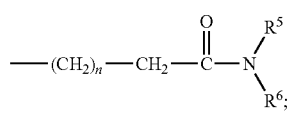

$Z^{15}$ is

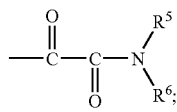

and
$Z^{16}$ is

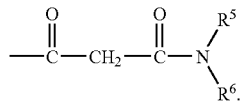

11. The compound of claim 10, wherein $R^6$ is hydrogen and n is 0 or 1.

12. The compound of claim 11, wherein $R^5$ is optionally substituted $C_{6-10}$ aryl or optionally substituted heteroaryl having 5-10 ring atoms.

13. The compound of claim 12, wherein $R^5$ is selected from the group consisting of phenyl, naphthyl, indenyl, isoindenyl, pyridyl, pyrimidinyl, pyrazinyl, pyridazinyl, triazinyl, pyrrolyl, pyrazolyl, benzothiazolyl, thiazolyl, imidazolyl, benzoimidazolyl, benzoxazolyl, indolyl, indazolyl, and benzotriazolyl, all of which can be optionally substituted.

14. The compound of claim 6, wherein $Z^1$ is selected from the group consisting of $Z^{17}$ and $Z^{18}$, wherein:

$Z^{17}$ is

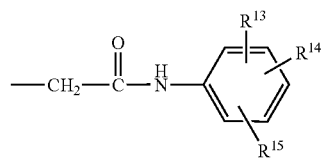

and
$Z^{18}$ is

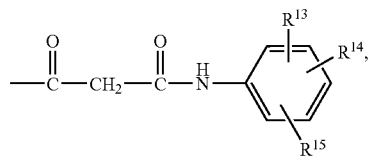

wherein $R^{13}$, $R^{14}$ and $R^{15}$ are each independently selected from the group consisting of hydrogen, alkyl, alkoxy, halogen, haloalkyl, hydroxy, hydroxyalkyl, cyano, amino, aminoalkyl, alkylamino, dialkylamno, hydroxyalkylamino, —C(O)OR$^{20}$, and —C(O)NR$^{20}$R$^{21}$, wherein R$^{20}$ and R$^{21}$ are each independently selected from the group consisting of hydrogen, alkyl, alkenyl, optionally substituted heterocyclo, optionally substituted cycloalkyl, optionally substituted aryl, optionally substituted arylalkyl, optionally substituted heteroaryl, optionally substituted heteroarylalkyl, and —CH$_2$—U—V, wherein U is CH$_2$, CHF, CF$_2$ or CHOH and V is hydrogen, alkyl, alkenyl or aryl.

15. The compound of claim 1, wherein Z is $Z^2$.

16. The compound of claim 15, wherein $Z^2$ is $Z^{21}$ having the structure:

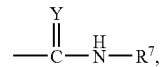

wherein Y is O or S and $R^7$ is selected from the group consisting of aryl and heteroaryl, either of which can be optionally substituted.

17. The compound of claim 16, wherein $R^7$ is optionally substituted $C_{6-10}$ aryl or optionally substituted heteroaryl having 5-10 ring atoms.

18. The compound of claim 17, wherein $R^7$ is selected from the group consisting of phenyl, naphthyl, indenyl, isoindenyl, pyridyl, pyrimidinyl, pyrazinyl, pyridazinyl, triazinyl, pyrrolyl, pyrazolyl, thiazolyl, imidazolyl, benzoimidazolyl, benzoxazolyl, indolyl, indazolyl, and benzotriazolyl all of which can be optionally substituted.

19. The compound of claim 18, wherein $R^7$ is unsubstituted phenyl or phenyl substituted with one, two, or three substituents each independently selected from the group consisting of alkyl, alkoxy, halogen, haloalkyl, hydroxy, hydroxyalkyl, cyano, amino, aminoalkyl, alkylamino, dialkylamino, and hydroxyalkylamino.

20. The compound of claim 1, wherein Z is $Z^3$.

21. The compound of claim 20, wherein $R^9$ and $R^{10}$ are each independently selected from the group consisting of
hydrogen;
hydroxyalkyl;
alkoxyalkyl;
cycloalkyl, and
phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy.

22. The compound of claim 20, wherein $R^9$ is hydrogen, alkyl, alkenyl, hydroxyalkyl, alkoxyalkyl, cycloalkyl, or phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; and $R^{10}$ is $R^{17}$—C(O)—, where $R^{17}$ is selected from the group consisting of optionally substituted benzyl and optionally substituted benzyloxy.

23. The compound of claim 20, wherein $R^9$ and $R^{10}$ together with the nitrogen atom to which they are attached form a 5- or 6-membered heterocyclic ring wherein one or more carbon atoms of the heterocyclic ring are optionally replaced with NR$^{18}$, O, or S, wherein R$^{18}$ is hydrogen or $C_{1-3}$ alkyl.

24. The compound of claim 20, wherein $R^{11}$ and $R^{12}$ are each independently selected from the group consisting of
hydrogen;
alkyl;
alkenyl;
hydroxyalkyl;
aminoalkyl;
cycloalkyl;
heterocyclo;
heterocycloalkyl;
phenyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;

benzyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy;

benzyloxyalkyl;

heteroaryl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy; and heteroarylalkyl optionally substituted with one or two substituents independently selected from the group consisting of alkyl, cycloalkyl, halogen, cyano, amino, alkylamino, dialkylamino, hydroxy, nitro, hydroxyalkyl, haloalkyl, and alkoxy.

25. The compound of claim 20, wherein $R^{11}$ and $R^{12}$ together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and =O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring; or wherein two adjacent carbon atoms of the $C_{3-7}$ cycloalkyl ring can form a bridge —O— to form a bicyclic ring; or wherein two adjacent carbon atoms of the $C_{3-7}$ cycloalkyl ring together form a fused phenyl group optionally substituted with alkyl, haloalkyl, amino, cyano, or hydroxy.

26. The compound of claim 20, wherein $R^{11}$ and $R^{12}$ together form =O.

27. The compound of claim 20, wherein $R^{12}$ is hydrogen, alkyl, or alkenyl; $R^9$ is hydrogen, alkyl, alkenyl, hydroxyalkyl, alkoxyalkyl, cycloalkyl, or phenyl optionally substituted with one substituent selected from the group consisting of alkyl, cycloalkyl, halogen, cyano, amino, alkylamino, dialkylamino, hydroxy, nitro, hydroxyalkyl, haloalkyl, and alkoxy; and $R^{10}$ and $R^{11}$ together form a bridge —$CH_2$—$CH_2$—$CH_2$— or —$CH_2$—$CHG^1$-$CHG^2$-$CH_2$—, wherein $G^1$ and $G^2$ are both hydrogen or together with the carbon atoms to which they are attached form a fused phenyl group.

28. The compound of claim 20, wherein $R^9$ is hydrogen and $R^{10}$ is hydrogen, hydroxyalkyl, or cycloalkyl.

29. The compound of claim 20, wherein $R^9$ and $R^{10}$ together with the nitrogen atom to which they are attached form a heterocyclic ring; $R^{11}$ is hydrogen, and $R^{12}$ is hydrogen, alkyl, cycloalkyl, heterocycloalkyl, or benzyl optionally substituted with one or two substituents each independently selected from the group consisting of alkyl, haloalkyl, halogen, hydroxy, hydroxyalkyl, alkoxy and cyano.

30. The compound of claim 20, wherein $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ is selected from the group consisting of hydrogen, alkyl, alkenyl, optionally substituted cycloalkyl, optionally substituted aryl, optionally substituted arylalkyl, optionally substituted heteroaryl, and optionally substituted heteroarylalkyl.

31. The compound of claim 20, wherein $R^9$ and $R^{10}$ together with the nitrogen atom to which they are attached form a heterocyclic ring to give $Z^{31}$ having the structure:

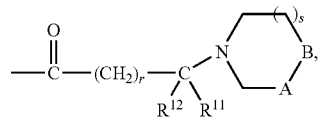

where
A is $CH_2$, CHF, $CF_2$ or CHOH;
B is $CH_2$, O, or N—$R^{51}$, where $R^{51}$ is $CH_3$ or $C(O)CH_3$;
s is 0, 1, or 2; and
r is 0 or 1.

32. The compound of claim 30, wherein $R^{11}$ and $R^{12}$ together form =O.

33. The compound of claim 30, wherein $R^{11}$ and $R^{12}$ are each independently selected from the group consisting of hydrogen, alkyl, and alkenyl or together with the carbon atom to which they are attached form a saturated or unsaturated $C_{3-7}$ cycloalkyl ring optionally substituted with one or more substituents each independently selected from the group consisting of alkyl, hydroxy, hydroxyalkyl, amino, carboxy, alkoxycarbonyl, alkylamino, dialkylamino, phenyl, and —O, wherein one or more carbon atoms of the $C_{3-7}$ cycloalkyl ring are optionally replaced with $NR^{19}$, O, S, or $SO_2$, wherein $R^{19}$ is hydrogen or $C_{1-3}$ alkyl, to form a heterocyclic ring.

34. The compound of 33, wherein $Z^3$ is $Z^{32}$ having the structure:

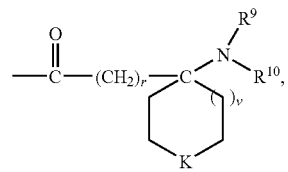

where K is selected from the group consisting of $CH_2$, O, S, $SO_2$, and $NR^{19}$, and v is 0, 1, or 2.

35. The compound of claim 20 having the Formula V:

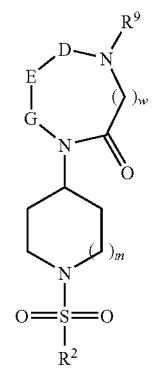

V wherein w is 1 or 2; D is $CH_2$, C(O), $CHCH_3$, $C(CH_3)_2$ or absent; E is $CH_2$, C(O), C(S), CHF, $CF_2$, or CHOH; and G is $CH_2$, C(O), $CHCH_3$, $C(CH_3)_2$ or absent.

36. The compound of claim 20, wherein Z is $Z^3$; $R^{11}$ and $R^{12}$ together form =O; $R^9$ is selected from the group consisting of alkyl, optionally substituted aryl, optionally substituted arylalkyl, optionally substituted heteroaryl, optionally substituted heteroarylalkyl, and —$CH_2$—U—V, wherein U is $CH_2$, CHF, $CF_2$ or CHOH and V is hydrogen, alkyl, or alkenyl; and $R^{10}$ and $R^1$ together form a bridge -D-E-G-, wherein D is $CH_2$, $C(O)$, $CHCH_3$, $C(CH_3)_2$ or absent; E is $CH_2$, $C(O)$, $C(S)$, $CHF$, $CF_2$, or $CHOH$; and G is $CH_2$, $C(O)$, $CHCH_3$, $C(CH_3)_2$ or absent.

37. The compound of claim 1, wherein $R^1$ is selected from the group consisting of hydrogen, $C_{1-6}$ alkyl, halo($C_{1-6}$)alkyl, $C_{1-4}$ alkoxy($C_{1-6}$)alkyl, halo($C_{1-4}$)alkoxy($C_{1-6}$)alkyl, hydroxy($C_{1-6}$)alkyl, amino($C_{1-6}$)alkyl, $C_{1-4}$ alkylamino($C_{1-6}$)alkyl, di($C_{1-4}$)alkylamino($C_{1-6}$)alkyl, and $C_{3-7}$ cycloalkyl.

38. The compound of claim 1, wherein $R^2$ is selected from the group consisting of
   a) cycloalkyl;
   b) aryl optionally substituted with one, two or three substituents each independently selected from the group consisting of alkyl, alkoxy, alkoxycarbonyl, cyano, halogen, haloalkyl, haloalkoxy, hydroxy, hydroxyalkyl, amino, alkylamino, dialkylamino, hydroxyalkylamino, —$C(O)OR^{20}$, and —$C(O)NR^{20}R^{21}$, wherein $R^{20}$ and $R^{21}$ are each independently selected from the group consisting of hydrogen, alkyl, alkenyl, optionally substituted heterocyclo, optionally substituted cycloalkyl, optionally substituted aryl, optionally substituted arylalkyl, optionally substituted heteroaryl, optionally substituted heteroarylalkyl, and —$CH_2$—U—V, wherein U is $CH_2$, $CHF$, $CF_2$ or $CHOH$ and V is hydrogen, alkyl, alkenyl or aryl;
   c) heteroaryl optionally substituted with one, two or three substituents each independently selected from the group consisting of alkyl, alkoxy, hydroxy, cyano, amino, alkylamino, dialkylamino, hydroxyalkylamino, alkoxycarbonyl, carboxy, alkylcarbonylamino, alkylcarbonylaminoalkyl, halogen, haloalkyl, phenyl, phenoxy, heteroaryl, and heterocyclo; and
   d) di($C_{1-6}$)alkylamino.

39. The compound of claim 38, wherein $R^2$ is phenyl or pyridyl optionally substituted with one or two substituents each independently selected from the group consisting of alkyl, alkoxy, halogen, haloalkyl, hydroxy, hydroxyalkyl, cyano, amino, alkylamino, dialkylamino and hydroxyalkylamino.

40. The compound of claim 38, wherein $R^2$ is phenyl substituted with alkyl, alkoxy, halogen, haloalkyl, hydroxy, hydroxyalkyl, cyano, amino, alkylamino, dialkylamino, hydroxyalkylamino, —$C(O)OR^{20}$, and —$C(O)NR^{20}R^{21}$, wherein $R^{20}$ and $R^{21}$ are each independently selected from the group consisting of hydrogen, alkyl, alkenyl, optionally substituted heterocyclo, optionally substituted cycloalkyl, optionally substituted aryl, optionally substituted arylalkyl, optionally substituted heteroaryl, optionally substituted heteroarylalkyl, and —$CH_2$—U—V, wherein U is $CH_2$, $CHF$, $CF_2$ or $CHOH$ and V is hydrogen, alkyl, alkenyl or aryl.

41. The compound as claimed in claim 1, wherein said compound is:
   N-(4-fluorophenyl)-2-[1-(3-trifluoromethyl-benzenesulfonyl)piperidin-4-ylamino]acetamide;
   2-{cyclopropyl-[1-(3-trifluoromethyl-benzenesulfonyl)-piperidin-4-yl]amino}-N-(4-fluorophenyl)acetamide;
   N-(4-fluorophenyl)-2-[1-(3-trifluoromethyl-benzenesulfonyl)-pyrrolidin-3-ylamino]acetamide;
   N-(3,5-bis-(trifluoromethyl)phenyl)-2-[1-(3-trifluoromethyl-benzenesulfonyl)piperidin-4-ylamino]acetamide;
   N-(2,4-difluorophenyl)-N'-[1-(3-trifluoromethyl-benzenesulfonyl)-piperidin-4-yl]malonamide; or
   a pharmaceutically acceptable salt thereof.

42. A pharmaceutical composition, comprising the compound of claim 1, or a pharmaceutically acceptable salt thereof, and a pharmaceutically acceptable carrier.

43. A method for ameliorating pain or hypertension in a mammal, comprising administering an effective amount of a compound of claim 1 or a pharmaceutically acceptable salt thereof, to a mammal in need of such amelioration.

44. The method of claim 43, wherein the method is for ameliorating pain.

45. The method of claim 44, wherein method is for palliative treatment of pain.

46. The method of claim 44, wherein said pain is selected from the group consisting of chronic pain, neuropathic pain, acute pain, and surgical pain.

47. A method of modulating calcium channels in a mammal, comprising administering to the mammal at least one compound of claim 1 or a pharmaceutically acceptable salt thereof.

48. The method of claim 47, wherein the N-type calcium channel is modulated.

49. A compound as claimed in claim 1, wherein the compound is $^3H$, $^{11}C$, or $^{14}C$ radiolabeled, or a pharmaceutically acceptable salt thereof.

50. A method of screening a candidate compound for the ability to bind to a receptor using a radiolabeled compound of claim 49, comprising a) introducing a fixed concentration of the radiolabeled compound to the receptor to form a mixture; b) titrating the mixture with a candidate compound; and c) determining the binding of the candidate compound to said receptor.

51. A method of preparing a pharmaceutical composition, comprising admixing a therapeutically effective amount of a compound of claim 1, or a pharmaceutically acceptable salt thereof, with a pharmaceutically acceptable carrier.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
caccatggtc cgcttcgggg ac                                            22

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer

<400> SEQUENCE: 2
ccgttcagtg gcctcctcc                                                19

<210> SEQ ID NO 3
<211> LENGTH: 23
<212> TYPE: DNA
```

<213> ORGANISM: Artificial Sequence
<220> FEATURE:
<223> OTHER INFORMATION: Synthetic Primer

<400> SEQUENCE: 3
ctagcaccag tgatcctggt ctg                                           23

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
agtgcgttgt gagcgcagta                                               20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
caccatggtc cagaagagcg g                                             21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
tctcagcgga tgtagacgcc t                                             21

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
caccatgtat gacgactcct ac                                            22

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
ggtggtcagt agctgtcctt agg                                           23

<210> SEQ ID NO 9
<211> LENGTH: 21
<212> TYPE: DNA
<213> ORGANISM: Artificial Sequence
<220> FEATURE:

```
<223> OTHER INFORMATION: Synthetic Primer

<400> SEQUENCE: 9
caccatggct gctggctgcc t                                           21

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
agagggtcac catagatagt gtctg                                       25

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
caccatgatt cgggccttcg ct                                          22

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
agcctgcgga ctacaggttg ctgac                                       25
```